US011583185B2

(12) United States Patent
Homyk et al.

(10) Patent No.: US 11,583,185 B2
(45) Date of Patent: *Feb. 21, 2023

(54) APPLICATIONS OF HYPERSPECTRAL LASER SPECKLE IMAGING

(71) Applicant: Verily Life Sciences LLC, Mountain View, CA (US)

(72) Inventors: Andrew Homyk, Belmont, CA (US); Jason Donald Thompson, Palo Alto, CA (US)

(73) Assignee: Verily Life Sciences LLC, Mountain View, CA (US)

(*) Notice: Subject to any disclaimer, the term of this patent is extended or adjusted under 35 U.S.C. 154(b) by 532 days.

This patent is subject to a terminal disclaimer.

(21) Appl. No.: 15/939,538

(22) Filed: Mar. 29, 2018

(65) Prior Publication Data

US 2018/0214025 A1 Aug. 2, 2018

Related U.S. Application Data

(63) Continuation of application No. 14/596,952, filed on Jan. 14, 2015, now Pat. No. 9,931,040.

(51) Int. Cl.
*A61B 5/00* (2006.01)
*A61B 5/026* (2006.01)
(Continued)

(52) U.S. Cl.
CPC .......... *A61B 5/0075* (2013.01); *A61B 5/0059* (2013.01); *A61B 5/0066* (2013.01);
(Continued)

(58) Field of Classification Search
CPC ..... A61B 5/0075; A61B 5/026; A61B 5/0295; A61B 5/02; A61B 5/0059; A61B 5/0082; A61B 5/72; A61B 5/0066; A61B 5/0261
See application file for complete search history.

(56) References Cited

U.S. PATENT DOCUMENTS 4,596,254 A 6/1986 Adrian et al.
5,090,416 A * 2/1992 Ogino .................. A61B 3/1225 351/216

(Continued)

FOREIGN PATENT DOCUMENTS

CN 101926644 B 12/2010
EP 0284248 A1 9/1988

(Continued)

OTHER PUBLICATIONS

Mahe, Guillaume, et al. "Laser speckle contrast imaging accurately measures blood flow over moving skin surfaces." Microvascular research 81.2 (2011): 183-188.

(Continued)

*Primary Examiner* — Sean D Mattson
(74) *Attorney, Agent, or Firm* — McDonnell Boehnen Hulbert & Berghoff LLP

(57) ABSTRACT

Systems and methods are provided for detecting the flow of blood or other fluids in biological tissue by illuminating the biological tissue with two or more beams of coherent light and detecting responsively emitted light. A difference in wavelength, coherence length, beam divergence, or some other property of the beams of illumination causes the beams to preferentially scatter from, be absorbed by, or otherwise interact with respective elements of the biological tissue. Flow properties in one or more regions of the biological tissue (e.g., a region with which both beams of light preferentially interact, a region with which only one of the beams preferentially interacts) could be determined based on detected responsively emitted light from the biological tissue. Variations in speckle patterns over time and/or space, Doppler shifts, or some other properties of the detected light could be used to determine the flow properties.

16 Claims, 12 Drawing Sheets

(51) Int. Cl.
*A61B 5/0295* (2006.01)
*A61B 5/02* (2006.01)

(52) U.S. Cl.
CPC .............. *A61B 5/0082* (2013.01); *A61B 5/02* (2013.01); *A61B 5/026* (2013.01); *A61B 5/0261* (2013.01); *A61B 5/0295* (2013.01); *A61B 5/681* (2013.01); *A61B 5/72* (2013.01)

(56) References Cited

U.S. PATENT DOCUMENTS 6,757,555 B2 6/2004 Kohayakawa
9,931,040 B2* 4/2018 Homyk .................... A61B 5/72
2002/0016533 A1* 2/2002 Marchitto ............ A61B 5/0071 600/310
2002/0030812 A1 3/2002 Ortyn et al.
2004/0233457 A1* 11/2004 Podoleanu ........... G01B 9/0201 356/479
2006/0203859 A1* 9/2006 Cable ...................... H01S 5/141 372/20
2007/0160279 A1* 7/2007 Demos ............... G01N 21/6486 382/133
2010/0081940 A1* 4/2010 McKenna ............. A61B 5/681 600/479
2012/0059245 A1 3/2012 Buschmann et al.
2012/0162438 A1* 6/2012 Thakor ................ A61B 5/0075 348/161
2012/0277559 A1 11/2012 Kohl-Bareis et al.
2013/0044771 A1 2/2013 Minneman et al.
2013/0144137 A1* 6/2013 Zalevsky ............. A61B 5/4875 600/314
2013/0223705 A1* 8/2013 Ferguson, Jr. ........ G06T 7/0012 382/128
2013/0292571 A1 11/2013 Mukherjee et al.
2014/0206980 A1 7/2014 Lee et al.

FOREIGN PATENT DOCUMENTS

EP 2565625 A1 3/2013
WO 2014/146053 A2 9/2014

OTHER PUBLICATIONS

International Search Report and Written Opinion of International Application No. PCT/US2016/012853 dated Apr. 26, 2016.
Luc Duteil et al., "A Double Wavelength Laser Doppler System to Investigate Skin Microcirculation", IEEE Transactions on Biomedical Engineering, vol. BME-19, No. 6, Jun. 1, 1985, pp. 439-447.
Jia Wang et al., "Dual-wavelength laser speckle imaging to simulataneously access blood flow, blood volume, and oxygenation using a color CCD camers", Optics Letters, vol. 38, No. 18, Sep. 15, 2013, pp. 3690-3692.

* cited by examiner

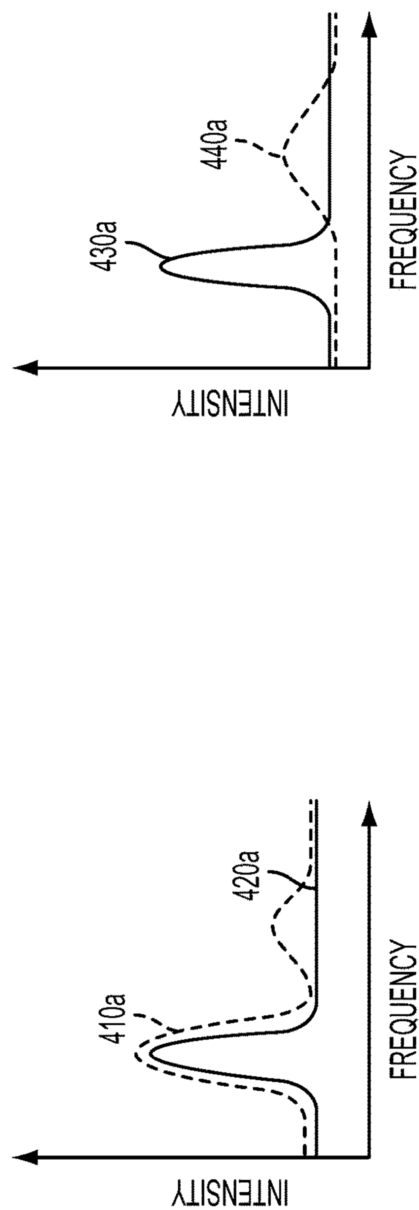
FIG. 4A
FIG. 4B
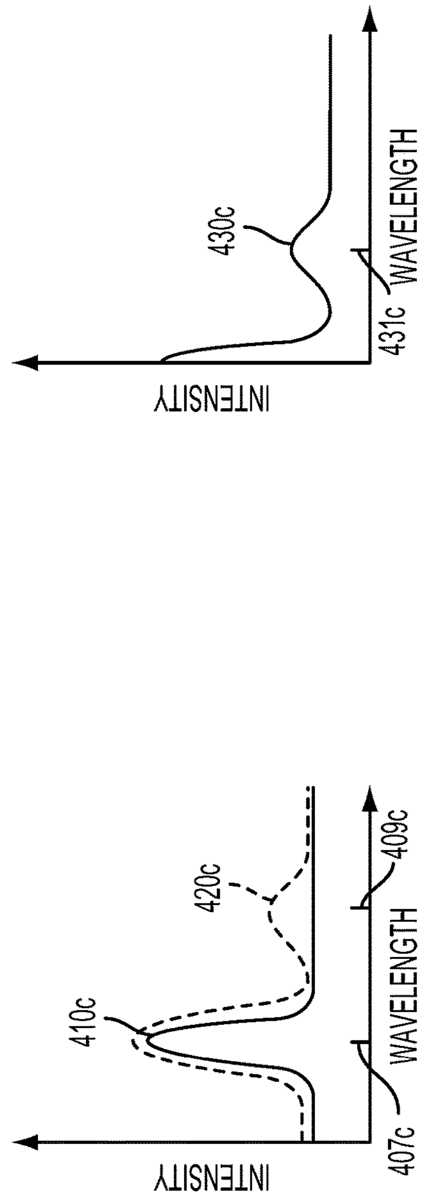
FIG. 4C
FIG. 4D

APPLICATIONS OF HYPERSPECTRAL LASER SPECKLE IMAGING

CROSS-REFERENCE TO RELATED APPLICATIONS

This application is a continuation of U.S. patent application Ser. No. 14/596,952, filed Jan. 14, 2015, which is incorporated herein by reference.

BACKGROUND

Unless otherwise indicated herein, the materials described in this section are not prior art to the claims in this application and are not admitted to be prior art by inclusion in this section.

Illumination of a scattering environment (e.g., an environment containing rough surfaces or other scattering objects or features) by a source of coherent, monochromatic light (e.g., a laser) can result in light emitted (i.e., reflected, refracted, diffracted, or otherwise scattered) from the environment forming a speckle pattern. That is, constructive and destructive interference between coherent, monochromatic light that takes different paths through the scattering environment due to scattering by features of the environment, and that thus experiences different path lengths, can form a pattern of light and dark speckles across a surface (e.g., across an array of light sensors). The speckle pattern can be related to the features of the scattering environment, such as the specific geometry of a rough surface and the locations, orientations, and properties of individual scattering objects (e.g., blood cells) in the environment. Additionally, interaction between monochromatic light and scatterers in the environment could cause the wavelength of the scattered light to be different from the wavelength of the illumination by an amount related to the Doppler effect.

SUMMARY

Some embodiments of the present disclosure provide a system including: (i) a light source, wherein the light source is configured to (a) emit a first beam of coherent illumination into a biological tissue and (b) emit a second beam of coherent illumination into the biological tissue, wherein the first and second beams differ with respect to at least one of wavelength, coherence length, or beam divergence; (ii) a light sensor configured to receive light from the biological tissue emitted in response to illumination by the light source; and (iii) a controller operably coupled to the light sensor and light source, wherein the controller includes a computing device programmed to perform controller operations including: (1) emitting the first beam of coherent illumination into the biological tissue using the light source; (2) detecting, using the light sensor, a first property of light received from the biological tissue in response to illumination by the first beam of illumination; (3) emitting the second beam of coherent illumination into the biological tissue using the light source; (4) detecting, using the light sensor, a second property of light received from the biological tissue in response to illumination by the second beam of illumination; and (5) determining at least one flow property in the biological tissue based on the first and second properties of the received light detected using the light sensor.

Some embodiments of the present disclosure provide a system including: (i) illumination means, wherein the illumination means are configured to (a) emit a first beam of coherent illumination into a biological tissue and (b) emit a second beam of coherent illumination into the biological tissue, wherein the first and second beams differ with respect to at least one of wavelength, coherence length, or beam divergence; (ii) sensing means configured to receive light from the biological tissue emitted in response to illumination by the illumination means; and (iii) controller means operably coupled to the sensing means and illumination means, wherein the controller means include a computing device programmed to perform controller operations including: (1) emitting the first beam of coherent illumination into the biological tissue using the illumination means; (2) detecting, using the sensing means, a first property of light received from the biological tissue in response to illumination by the first beam of illumination; (3) emitting the second beam of coherent illumination into the biological tissue using the illumination means; (4) detecting, using the sensing means, a second property of light received from the biological tissue in response to illumination by the second beam of illumination; and (5) determining at least one flow property in the biological tissue based on the first and second properties of the received light detected using the sensing means.

Some embodiments of the present disclosure provide a method including: (i) emitting a first beam of coherent illumination into a biological tissue; (ii) detecting a first property of light received from the biological tissue in response to illumination by the first beam of illumination; (iii) emitting a second beam of coherent illumination into the biological tissue, where the second beam differs from the first beam with respect to at least one of wavelength, coherence length, or beam divergence; (iv) detecting a second property of light received from the biological tissue in response to illumination by the second beam of illumination; and (v) determining at least one flow property in the biological tissue based on the detected first and second properties of the received light.

These as well as other aspects, advantages, and alternatives, will become apparent to those of ordinary skill in the art by reading the following detailed description, with reference where appropriate to the accompanying drawings.

BRIEF DESCRIPTION OF THE DRAWINGS

FIG. 4A illustrates frequency content of signals emitted from a biological tissue in response to illumination by two beams of coherent illumination.

FIG. 4B illustrates first and second peaks corresponding to first and second signals determined based on the frequency content illustrated in FIG. 4A.

FIG. 4C illustrates spectrographic content of signals emitted from a biological tissue in response to illumination by two beams of coherent illumination.

FIG. 4D illustrates spectrographic content determined based on the spectrographic content illustrated in FIG. 4C.

DETAILED DESCRIPTION

Figure 1:
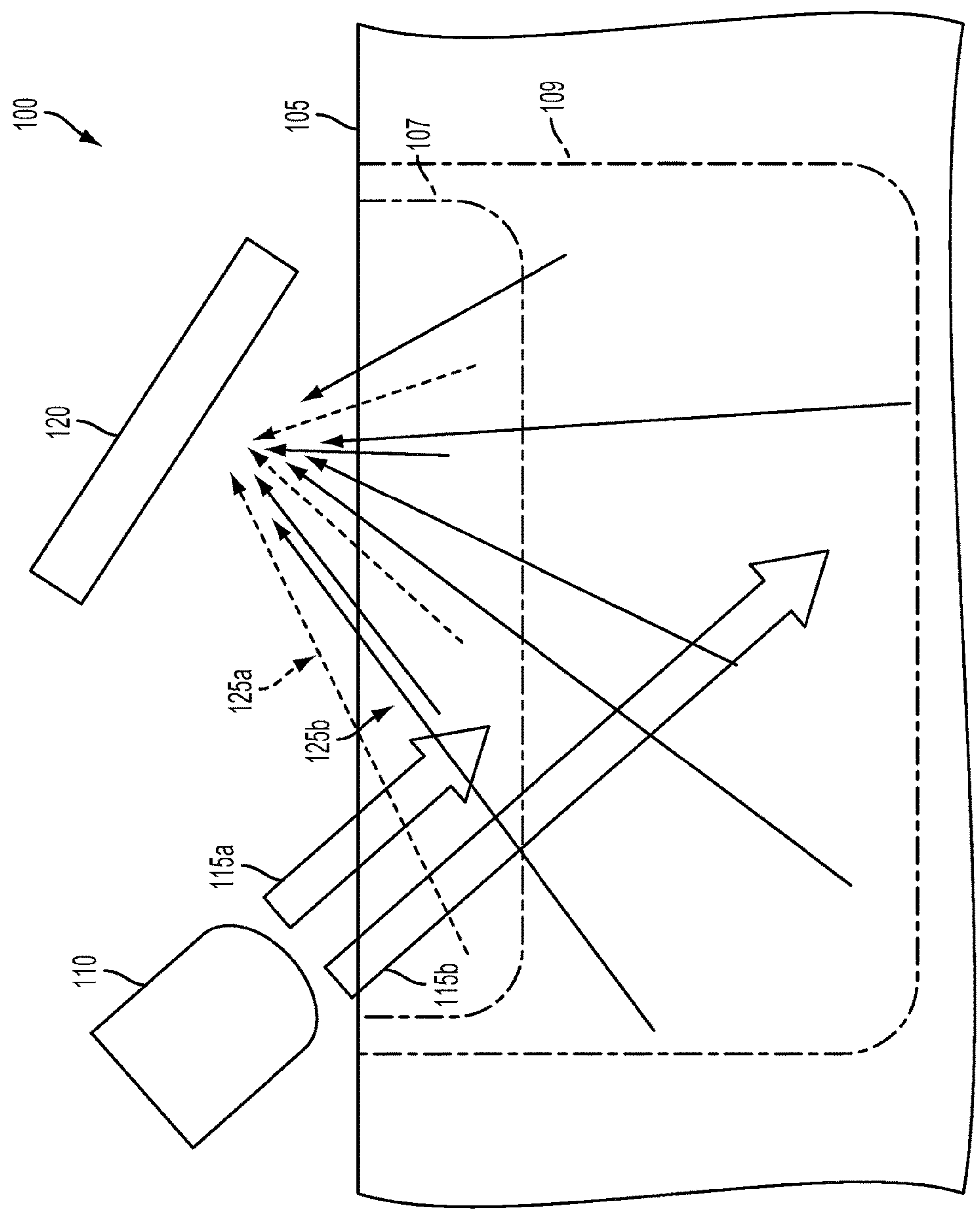
FIG. 1 is a side partial cross-sectional view of an example system, while measuring fluid flow in biological tissue.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Further, while embodiments disclosed herein make reference to use on or in conjunction with a living human body, it is contemplated that the disclosed methods, systems and devices may be used in any environment where detection of flow properties (e.g., determining a map of flow properties across an area and/or within a volume) is desired. The environment may be any living or non-living body or a portion thereof, a gel, an emulsion, a fluid conduit, a fluid reservoir, etc. For example, one of skill in the art will recognize that the embodiments disclosed herein may be used to sense properties of fluid flow in a microfluidic system. Moreover, while the present disclosure describes embodiments for use in vivo, one of skill in the art will also recognize that in vitro applications are possible as well. Accordingly, the environment may also include a test tube or other vessel for holding a fluid.

I. Overview

A property of flow in an environment (e.g., a mean velocity of a fluid flow in an environment, a peak velocity of scatterers in an environment, a distribution of velocities of scatterers in an environment) can be detected by illuminating the environment using beams of substantially coherent, monochromatic light emitted by one or more light sources (e.g., lasers) and detecting one or more properties (e.g., a time-varying pattern of constructive and destructive interference, a degree of frequency shift) of light emitted by the environment in response to the illumination. That is, scattering of the illumination by scattering elements in the environment (e.g., cells in blood, smoke particles in air) could cause the light responsively emitted from the environment to have one or more properties related to the movement of the scattering elements. A light sensor could be configured to detect the intensity, frequency, wavelength, or some other property of light emitted by the environment at one or more points in time in response to the illumination and the detected property could be used to determine the velocity of the scatterers, the mean flow rate of fluid containing the scatterers, or some other flow property in the environment.

Multiple such beams of coherent, monochromatic illumination that differ with respect to one or more properties (e.g., different wavelengths, different coherence lengths, different angles relative to a target environment, different beam divergences, different beam shapes, different spectral line widths) could selectively interact with respective different elements of a biological tissue or other environment. For example, multiple different beams of illumination could selectively and/or preferentially interact with biological tissue within multiple ranges of depths beneath a surface of the biological tissue (e.g., longer-wavelength light could penetrate deeper into the tissue than shorter-wavelength light, and thus preferentially interact with both shallow and deep tissues). In some examples, multiple beams of illumination could selectively interact with respective structures or types of tissue within the biological tissue (e.g., a first beam could have a wavelength of other specified property to interact selectively with blood, while a second beam could interact nonspecifically with the biological tissue, or could interact selectively with non-blood portions of the biological tissue). Light emitted responsive to each of multiple different beams of illumination could be detected and used to determine relative or absolute flow properties in different portions of biological tissue, e.g., to determine the flow rate of blood relative to non-blood tissue, to determine flow properties in tissue at a particular depth, to determine flow properties in a specified type of tissue, to determine overall movement or displacement of tissue.

Flow properties in biological tissue could be determined in a variety of ways based on a variety of different detected properties of light received from the biological tissue in response to illumination by one or more beams of illumination. Changes in a detected level of intensity of light received by a light sensor over time (i.e., a time-varying pattern of constructive and destructive interference in the light emitted by the environment) could be used to determine a plurality of flow properties in the environment. For example, the duration, rise time, fall time, and/or some other property of pulses, transitions, or other features of a time-varying intensity of light received by a particular light-sensitive element could be related to a flow property (e.g., a flow rate of blood cells) or other property of motion (e.g., overall motion or displacement) in or near a portion of the environment from which the light sensor received the light. Additionally or alternatively, changes in a frequency, wavelength, phase, or other spectral property of light received from the environment relative to properties of the beam of illumination causing the environment to emit the received light could be detected (e.g., using a spectrometer, an optical heterodyne detector, an interferometer) to determine flow properties or other information about the environment (e.g., to determine a velocity of scatterers in the environment based on a Doppler shift in the received light due to scattering of the beam of illumination by the moving scatterers, to determine an overall motion or displacement of the environment relative to a sensor or light emitter). Flow properties could be determined for a plurality of points or regions in an environment to allow for a variety of applications, for example, to determine a flow map of fluid flows in the environment, to detect the presence, shape, width, pattern, or other information about vasculature in the environment, to detect a tumor or other target in the environment, or some other application(s).

The environment could be any environment that, when illuminated by a laser or other source of substantially coherent light, emits light having one or more detectable properties. The one or more detectable properties could include, for example, a pattern of constructive and destructive interference (e.g., a speckle pattern), a degree of Doppler shift, or any other property of the emitted light that can be related to a flow property of one or more regions of the environment (e.g., a velocity of flow of a fluid in the environment, an overall motion of the environment and elements thereof). The environment could include gases, liquids, gels, or other fluids. The environment can include a population of scattering agents, i.e., small particles or other objects or features that can move with a fluid flow and reflect, refract, diffract, or otherwise scatter light. In some examples, the environment could be a biological environment that includes blood cells, portions of vasculature, and other tissues. For example, the environment could be a biological tissue in a surgical environment that is subject to a surgical intervention, e.g., to an intervention that includes cutting, ablating, ligating, cauterizing, or otherwise manipulating or interacting with regions of the biological tissues according to an application.

Changes in the arrangement of scattering agents or other scattering features within the environment and/or movement or displacement of the environment can cause a change in one or more properties of light (i.e., a speckle pattern, a wavelength or other spectral property) emitted from the environment in response to coherent illumination. For example, displacement of scattering features (e.g., blood cells) disposed in a fluid (e.g., blood in a portion of vasculature, interstitial fluid in a tumor) due to flow of the fluid can cause a change in the pattern of emitted light that is related to the direction, velocity, or other properties of the fluid, the fluid flow, and/or the location and/or orientation of the scattering features. When intensity of light emitted from a particular region (e.g., from an area of the environment corresponding to the field of view of a light sensor or other imager) is measured over time, time dependent features of the measured intensity (i.e., a waveform of the measured intensity) can be related to a flow property and/or other properties of the environment within and/or proximate to the particular region. In another example, displacement of scattering features (e.g., blood cells) disposed in a fluid (e.g., blood in a portion of vasculature, interstitial fluid in a tumor) due to flow of the fluid can cause a change in the wavelength of light emitted from the scatterer relative to the light that illuminated the scatterer (e.g., due to the Doppler effect) that is related to the direction, velocity, or other properties of the location and/or orientation of the scattering features. A frequency or other spectrographic properties of light emitted from a particular region (e.g., from an area of the environment corresponding to the field of view of a light sensor or other imager) could be detected and related to a flow property and/or other properties of the environment within and/or proximate to the particular region.

For example, movements of blood cells proximate to the particular region can cause a corresponding light sensor to experience a "speckle event" in which the intensity of the light received by the light sensor from the environment increases/decreases suddenly, followed by a sudden decrease/increase. One or more properties of the speckle event pulse (e.g., a rise time, a fall time, a pulse width, a pulse amplitude) could be related to a flow property (e.g., a velocity of an individual blood cell in a blood or interstitial fluid flow or a distribution of velocities of individual blood cells in a blood or interstitial fluid flow) of the environment. Other properties (e.g., a rate of change) of the measured intensity level or other measured properties (e.g., a spectrographic content) of the received light over time could be related to flow properties of the environment. For example, an average intensity could be detected, over a period of time (e.g., during an exposure) by the light sensor. Such a detected average intensity could be related to a frequency of speckle events or some other property of the particular region. Such a detected average intensity, a relationship between such average intensities measured across a region (e.g., a contrast value determined for a region based on detected average intensity values for the region, i.e., a spatial contrast), or some other detected property of one or more intensities or other detected properties of detected light from one or more portions of the environment could be used to determine flow properties of the environment.

An environment of interest (e.g., a biological tissue) could be illuminated by multiple beams of coherent illumination differing in one or more properties as to allow various applications as described herein. In some examples, such multiple beams of coherent illumination could be emitted at the same time, e.g., by operating multiple corresponding light source (e.g., lasers) to illuminate an environment at the same time. Additionally or alternatively, one or more light sources could be operated to emit the multiple beams of illumination during respective different periods of time. In some examples, this could include operating a single light-emitting element (e.g., a single laser) to emit multiple beams of illumination differing in one or more properties during respective different periods of time. For example, such a light source could include a tunable laser (e.g., a laser configured to control a wavelength of a beam of coherent light emitted by the laser by altering a cavity length, a gain medium refractive index, a Bragg reflector passband, or some other property of the laser) that could be configured to emit a beam of coherent light having a first wavelength during a first period of time and a second, different wavelength during a second period of time. In some examples, a light source could include a laser configured to control a coherence length of the beam of emitted illumination (e.g., a laser configured to detune a cavity of the laser, to change a refractive index of one or more elements of the laser, to inject a carrier into the laser, to modulate the laser output at a high frequency) that could be configured to emit a beam of coherent light having a first coherence length during a first period of time and a second, different coherence length during a second period of time. Other properties (e.g., angles relative to an environment of interest, beam divergences, etc.) could differ between beams of coherent illumination emitted into an environment of interest.

In some embodiments, the above described system may be implemented as a stationary measurement device that may be brought into contact or proximity with a target environment. For example the system could be configured to emit beams of coherent light toward a biological tissue undergoing a surgical intervention, and to determine flow properties of the biological tissue based on received light emitted from the biological tissue responsive to the multiple beams of illumination. Such determined flow properties could be used to map vasculature in the biological tissue, to detect the presence and/or location of a tumor in the biological tissue, or to determine some other information about the biological tissue. Such information could be presented (e.g., via a display, via an augmented reality device, via a control console of a robotic surgical system) to a surgeon. Additionally or alternatively, such information could be used to operate an automated or semi-automated robotic surgical system (e.g., to inform the ablation of a tumor detected in the tissue while avoiding causing damage to vasculature in the tissue). In some embodiments, the above described system could be implemented as a wearable device and configured to detect flow properties through the skin of a wearer, e.g., to determine a flow rate over time of blood in portions of vasculature of a wearer. In other embodiments, the above described system may be implemented to interrogate an environment that is not a part of a human body, e.g., an in vitro or other sample container, an outdoor environment, an animal body, or some other environment of interest that can scatter or otherwise interact with emitted beams of coherent illumination in a manner related to flow properties of the environment.

It should be understood that the above embodiments, and other embodiments described herein, are provided for explanatory purposes, and are not intended to be limiting.

II. Illustrations of Flow Properties and Scattering of Coherent Light in Biological Tissues Flow properties (e.g., flow rates at a plurality of locations) of fluid in an environment (e.g., blood in a portion of vasculature and/or interstitial space, a liquid, gel, emulsion, gas, or other flowing material in an industrial or other environment) can be detected by a variety of methods related to properties of the fluid and of the environment. In examples wherein the environment contains scatterers (i.e., particles that can scatter incident illumination and that can be affected by a fluid or other flow in the environment) or other reflective and/or refractive boundaries, flow properties of the environment could be detected and/or determined by illuminating the environment with coherent illumination and detecting a wavelength shift of, a spectrographic property of, a time- and/or space-dependence of a pattern, intensity, or other property of constructive and destructive interference in, or some other property of light scattered by the scatterers and emitted from the environment in response to illumination. Further, two or more beams of such coherent illumination, differing in one or more properties (e.g., having different wavelengths, coherence length, beam divergences) could be used to illuminate the environment and the allow determination of flow properties in the environment based on received light emitted from the environment responsive to such beams of illumination.

First and second (or more) beams of light differing in one or more properties (e.g., having respective different wavelengths) could preferentially interact with respective elements of an environment of interest (e.g., a biological tissue) to allow the detection of flow properties in the environment. For example, first and second beams of light could preferentially interact with (e.g., be differently scattered, reflected, transmitted, absorbed, or otherwise interact with) respective first and second sets of elements in the environment (e.g., a first set of elements comprising the blood in vasculature of a biological tissue, and a second set comprising non-blood tissues of the biological tissue), elements within respective first and second ranges of depths within the environment (e.g., a first beam could preferentially interact with biological tissue within a shallow depth of a surface of the tissue, and a second beam could interact with deeper tissue in addition to the shallow tissue), or according to some other pattern. Light received from the environment in response to such illumination could be used to determine flow properties in the environment, e.g., to determine a flow property in elements of the environment that preferentially interact with both of the beams of illumination and/or elements that only preferentially interact with one of the beams. Additionally or alternatively, first and second (or more) beams of illumination could interact with substantially the same elements/regions of an environment of interest but could interact with the environment in a different way such that detection of first and second lights received from the environment responsive to respective beams of illumination could allow determination of flow properties in the environment.

FIG. 1 is a cross-sectional view through biological tissue 105 illustrating the operation of an example system 100. In the example shown in FIG. 1, the system 100 includes a light source 110 configured to emit first 115*a* and second 115*b* beams of coherent illumination into the biological tissue 105. The first 115*a* and second 115*b* beams of illumination preferentially interact with respective first 107 and second 109 regions of the biological tissue 105. The first 107 and second 109 regions of the biological tissue correspond to elements of the biological tissue 105 within respective first and second ranges of depths within the biological tissue (e.g., shallow tissue in region 107 and deeper tissue in region 109). The system 100 additionally includes a light sensor 120 configured to receive first 125*a* and second 125*b* light emitted from the biological tissue 105 in response to illumination by the first 115*a* and second 115*b* beams of illumination, respectively. The first 125*a* and second 125*b* emitted lights are emitted from respective first 107 and second 109 regions of the biological tissue 105. The system 100 additionally includes a controller (not shown) configured to operate the light source 110 and the light sensor 120 and to determine at least one flow property (e.g., a flow rate of blood in shallow regions (e.g., 107) of the biological tissue 105) of blood cells or other scattering elements in the biological tissue 105. The system 100 could include further elements, e.g., a housing within which the light source 110, light sensor 120, and/or controller could be disposed, a mount configured to mount the light source 110 and light sensor 120 to an arm or to other elements of anatomy of a person or to some surgical equipment or system, or to some other elements.

Preferential interaction between a beam of illumination and elements of an environment of interest (e.g., biological tissue 105) includes the beam and/or elements having one or more properties such that light emitted from the environment responsive to the beam of illumination has one or more properties (e.g., a time-varying pattern of constructive and destructive interference, a change in wavelength of the emitted light relative to a wavelength of the illumination) related to one or more properties of the elements of the environment (e.g., properties related to a flow property in the environment). In some examples, this could include the elements of the environment having a transmittance, absorbance, degree of scattering, or some other optical property related to one or more properties of the beam of illumination (e.g., a wavelength-dependence). For example, the environment 105 could have a wavelength-dependent absorbance such that beams of illumination having different wavelengths (e.g., 115*a*, 115*b*) are absorbed at different rates and/or penetrate the environment to different depths. The beams of illumination could additionally be scattered and/or reflected by the elements of the environment and emitted from the environment (e.g., toward a light sensor 120). Thus, light emitted from the environment responsive to the beam of illumination could be related to properties (e.g., flow properties) of elements of the environment with which the beam of illumination preferentially interacts.

As an example, the first 115*a* and second 115*b* beams of illumination could have respective wavelengths, and the biological tissue 105 could have a wavelength-dependent attenuation coefficient or other measure of absorption of illumination. Thus, first light 125*a* emitted from the biological tissue 105 in response to illumination by the first beam 115*a* could be emitted from the first region 107 and have one or more properties related to the first region 107 (e.g., related to flow properties in the first region 107). This could be due to absorption of the first beam of illumination 115*a* in the biological tissue 105 causing the first beam of illumination 115*a* to penetrate and illuminate elements of the biological tissue 105 contained in the first region 107, absorption of light scattered and/or reflected light from elements of the biological tissue 105 deeper than the first region 107 due to the first beam 115*a* such that such scattered or reflected light is not part of the first emitted light 125*a*, or some combination of mechanisms. Similarly, second light 125*b* emitted from the biological tissue 105 in response to illumination by the second beam 115*b* could be emitted from the second region 109 and have one or more properties related to the second region 109.

Preferential interaction could additionally or alternatively include first and second (or more) beams of light having different interactions with the same elements of an environment. For example, first and second beams of illumination could illuminate the same element (e.g., a blood cell or other scatterer) of an environment, and light from both beams could be scattered and/or reflected from the element to be emitted from the environment and detected by a light sensor. A difference between the first and second beams (e.g., a wavelength difference) could result in a difference in the interaction with the element (e.g., a difference in the angle of reflection/scattering of light reflected/scattered by the element, a difference in the degree of reflection/scattering of the beams of light relative to changes in orientation of the element) such that respective responsively emitted lights could have respective different properties (e.g., different time-varying patterns of intensity, different intensity frequency spectra) that could be detected and used to determine flow properties in the environment.

Emitted light (e.g., emitted light 125*a* and 125*b*) from the biological tissue 105 could include patterns of constructive and destructive interference, changes in wavelength relative to a respective beam of illumination, or other properties related to individual portions of a respective beam of coherent illumination (e.g., beams 115*a* and 115*b*) being scattered by different scattering (e.g., reflecting, refracting, diffracting) elements in the biological tissue 105 (e.g., cell walls, blood cells, cell elements, tissue boundaries, chromophores, fat globules, or other reflective elements/boundaries and/or discontinuities in refractive index). Thus, different portions of the coherent illumination (e.g., 115*a*, 115*b*) could experience different path lengths between emission at the light source 110 and reception at the light sensor 120. The different portions of the beam of coherent illumination are thus out of phase and will constructively and/or destructively interfere with each other in a manner related to respective amplitudes and relative phases of the portions of the emitted light (e.g., 125*a*, 125*b*) to form a pattern of constructive and destructive interference at the light sensor 120 and/or at other locations in the vicinity of the system 100 and biological tissue 105. Additionally or alternatively, such scattering events could change a wavelength and/or spectrum of the coherent illumination in a manner related to an absolute or relative translational and/or rotational velocity of a scattering element. Portions of the beam of coherent illumination scattered in such a way could result in portions of the emitted light (e.g., 125*a*, 125*b*) having wavelengths, spectra, or other spectrographic properties that are different relative to a respective beam of illumination (e.g., 115*a*, 115*b*).

Other properties of light emitted from an environment in response to illumination by a beam of coherent illumination could be related to other properties (e.g., flow properties) of elements of the environment in other ways. Further, illuminating light (e.g., light emitted by the light source 110 as part of first 115*a* or second 115*b* beams of illumination) could be scattered or otherwise interact with elements of the environment multiple times before being emitted from the environment (e.g., emitted toward the light sensor 120 as emitted light 125*a* or 125*b*). As a result, such multiply-scattered light could have one or more properties (e.g., a phase difference, a path length, a wavelength) related to multiple elements and/or regions of the environment with which it interacted (e.g., from which it was scattered).

Two or more beams of illumination (e.g., 115*a*, 115*b*) could differ in one or more of a variety of properties. The beams could have respective different wavelengths, spectra, spectral line widths, coherence lengths, beam dispersions, angles relative to an environment of interest, beam cross-sections or shapes, patterns of structured illumination, or other properties. Such differences in one or more properties of two or more beams of illumination could result in the two or more beams of illumination being differently absorbed, scattered, transmitted, refracted, shifted in wavelength (e.g., via the Doppler effect), or otherwise differently interacting with elements of the environment. As a result, the two or more beams of illumination could preferentially interact with different elements (e.g., different tissues, elements within different regions, elements within different respective depths) in the environment and/or could be differently affected (e.g., could experience different changes in wavelength, could be scattered at different angles) by the same or different elements in the environment.

An environment of interest could be illuminated by multiple such different beams of illumination during different respective periods of time or could be illuminated simultaneously. For example, a first beam of illumination could be emitted during a first period of time, and a second beam of illumination could be emitted during a second period of time. A light sensor could receive first and second lights responsively emitted from the environment during the first and second periods of time, respectively. This could include operating one or more light-sensitive elements of the light sensor to receive both the first and second emitted lights (e.g., a single phototransistor, photodiode, or other light-sensitive element could be used, during the first and second periods of time, to detect one or more properties of the first and second emitted lights). Additionally or alternatively, different sets of one or more light sensitive elements of the light sensor could be operated to receive the first and second emitted lights. This could include the first and second emitted lights differing in wavelength or some other spectrographic property, and first and second sets, respectively, of one or more light-sensitive elements of the light sensor being configured to detect light having the respective different wavelengths or other spectrographic properties (e.g., by the first and second sets of light-sensitive elements having respective different filters configured to pass respective different bands of wavelengths of light, being disposed at respective different locations within a spectrometer, e.g., relative to a diffraction grating, prism, or other optically dispersive element).

Such differently configured sets of light-sensitive elements could additionally or alternatively be operated to detect different lights emitted from an environment of interest in response to illumination of the environment by respective different beams of illumination simultaneously. Further, different beams of illumination could be emitted by elements of a light source in common (e.g., beams having different wavelengths or coherence lengths could be emitted by a tunable laser or other type of laser during respective different periods of time). Additionally or alternatively, a light source could include multiple different elements or sets of element configured to emit respective different beams of illumination (e.g., multiple different lasers configured to emit respective different beams of illumination having respective different wavelengths) during respective different periods of time or simultaneously.

Emitted lights received from an environment of interest in response to illumination by respective different beams of illumination could be used in a variety of ways to determine flow properties in the environment. In some examples, different beams of illumination could preferentially interact with respective different regions and/or elements of the environment (i.e., different lights emitted from the environment in response to illumination by respective beams of illumination could have properties related to respective different regions and/or elements of the environment) and respective detected emitted lights could be used to determine flow or other properties within the respective different regions. Such determined flow information could be used to determine a flow property (e.g., a flow rate, a velocity of fluid in a flow) in a first region/of first elements relative to a second region/second elements.

In some examples, detected light emitted in response to a first beam of illumination could be used to remove a noise, to reject a common-mode signal, or to otherwise affect the determination of a flow property in the environment based on detected light emitted in response to a second beam of illumination. This could include determining respective first and second flow properties based on first and second received emitted lights (e.g., flow properties in corresponding different regions of an environment) and determining a flow property in the environment based on the first and second determined flow properties. For example, a flow property of a first set of elements in the environment relative to a second set of elements in the environment could be determined by removing a baseline velocity of the environment (e.g., due to relative motion between the environment and a light source/light sensor configured to illuminate/detect light emitted from the environment) from a measure of the velocity of a fluid flow within the environment.

In another example, a flow property (e.g., a distribution of velocities of blood cells in a portion of subsurface vasculature) of a first region of the environment that includes elements of interest (e.g., the blood cells, in addition to other elements of a body, e.g., blood vessel walls, skin, fat) relative to a second set of elements in the environment that does not include the elements of interest (e.g., a set of elements that includes the elements included in the first set of elements except the blood cells) could be determined by removing some unwanted signal (e.g., a distribution of velocities of non-blood-cell elements of the environment) determined from light received from the second set of elements from a signal (e.g., a distribution of velocities of blood cell and non-blood-cell elements of the environment) determined from light received from the first set of elements. Other methods of determining flow properties in an environment based on emitted lights received from the environment in response to different beams of illumination, or based on flow properties of different region/element of the environment determined therefrom, are anticipated.

A variety of different properties of emitted light received from an environment of interest in response to a beam illumination (e.g., an intensity, an orientation or direction of polarization, a wavelength, a spectrum, a spectral line width, a relative phase, or some other properties at one or more points in time) could be detected (e.g., by a light sensor 120) and used to determine, individually or in combination with other emitted lights received from the environment in response to illumination by other beams of illumination, flow properties in the environment. In some examples, time-varying patterns of constructive and destructive interference (e.g., speckle events, spatial contrast) in light emitted from a particular portion (e.g., from a region and/or set of elements of the environment with which a related beam of illumination preferentially interacts) of an environment of interest could be related to changing properties of the particular portion of the environment of interest. The relationship between the time-varying patterns in the emitted light and the changing properties of the particular portion could be related to a depth of the portion within the environment, a distance between the portion and a surface via which the light is emitted, a coherence length and/or wavelength of the beam of illumination applied to the environment, or some other properties of the portion, the beam of illumination applied to the environment, and/or a light sensor or other sensor(s) used to receive light responsively emitted from the environment.

In some examples, a wavelength, spectrum, linewidth, or other spectrographic information of light emitted from a particular portion (e.g., from a region and/or set of elements of the environment with which a related beam of illumination preferentially interacts) of an environment of interest could be related to properties of the particular portion of the environment of interest. For example, a difference in the wavelength of the light received from a portion of the environment relative to a wavelength of a corresponding beam of illumination could be related to a velocity of scatterers (e.g., blood cells) in the environment that scattered or otherwise interacted with the beam of illumination to cause the received light to be emitted. Additionally or alternatively, a center frequency, a peak width, a line width, a shape of a peak, or some other property of a spectrum of the received light could be related to an absolute or relative (e.g., relative to the velocity of other elements in the environment, relative to the motion of the environment relative to a source of illumination and/or a light sensor) velocity of elements in the environment, a distribution of such velocities, or some other flow property in the environment.

Thus, time-varying or static patterns of constructive and destructive interference, intensities, wavelengths, linewidths, optical spectra, or other information or properties of the emitted light (e.g., 125*a*, 125*b*) could be related to a configuration of elements of the biological tissue 105 (e.g., to the location of blood cells or other elements in the first 107 and/or second 109 regions, respectively). The light sensor 120 detecting such properties could include the light sensor 120 being configured and/or operated to detect any property or properties of emitted light (e.g., 125*a*, 125*b*) from the biological tissue 105 having a time dependence or other property that can be used to determine flow properties of blood or other fluids in the biological tissue 105. In some examples, this could include individual light-sensitive elements (e.g., 125*a*, 125*b*) of the light sensor 120 being configured to detect the intensity, wavelength, spectrum, and/or some other property of the emitted lights 125*a*, 125*b* at a plurality of points in time. For example, the intensity could be detected at a sufficiently high rate to detect the presence or other properties of individual speckle events or other short-duration features of the detected intensity.

Additionally or alternatively, information about time-varying patterns of constructive and destructive interference or other properties of the received light could be detected by filtering, integrating, or otherwise performing some analog operations on light received by the light sensor 120 (e.g., by individual light-sensitive elements of the light sensor 120). For example, an average intensity of a received light (e.g., 125*a*, 125*b*) during a specified period of time (e.g., during an exposure having a specified duration between, e.g., approximately 10 milliseconds and approximately 20 milliseconds and occurring during a period of time when the biological tissue 105 is being illuminated by one or both of the beams of illumination 125*a*, 125*b*) could be detected and used to determine flow properties in the biological tissue 105. In another example, a power of a detected intensity, intensity within a specified range of wavelengths of light, or time-varying property of the received light within a specified range of temporal frequencies could be determined by filtering the detected property (e.g., filtering by analog electrical circuits and/or by sampling the detected property at a sufficiently high rate and operating a controller to apply the filter computationally) and relating the determined power to flow properties in the biological tissue 105. Further, such detected time-varying patterns corresponding to a plurality of different portions of tissue (e.g., detected using a corresponding plurality of light-sensitive elements of the light sensor 120 configured as a camera) could be combined to determine flow properties of the biological tissue 105 (e.g., by determining a spatial contrast in images of the biological tissue 105 detected using the light sensor 120 based on light emitted from the biological tissue 105 in response to illumination by one or both of the beams of illumination 115*a*, 115*b*).

In some examples, the light sensor 120 could include a camera (i.e., could include an aperture, an array of light-sensitive elements, and/or optics) and receiving the light from the biological tissue 105 (e.g., 125*a*, 125*b*) could include detecting the intensity or other properties of the emitted light that is received by the camera from various respective angles relative to the camera. Alternatively, the light sensor 120 could include a plurality of light-sensitive elements configured to receive light from respective portions of biological tissue by other means. In some examples, the individual light-sensitive elements could include baffles, coded apertures, diffraction gratings, angle-sensitive pixels (e.g., pixels of a planar Fourier capture array), or other elements configured such that individual light-sensitive elements receive light from a specified portion of tissue (e.g., at a specified angle(s) and/or specified location(s) relative to the light sensitive-element). Other configurations and operations of one or more light sensors (e.g., 120) to detect properties (e.g., time-varying patterns of constructive and destructive interference, differences in wavelength relative to specified wavelengths of corresponding beams of illumination) in light emitted from an environment (e.g., 105) in response to illumination by two or more beams of illumination are anticipated.

Two or more beams of illumination could differ with respect to one or more properties in a variety of ways such that the beams of illumination preferentially interact with respective elements of an environment to provide determination of flow properties in the environment based on properties of light emitted from the environment responsive to the illumination. As illustrated in FIG. 1, two beams of illumination 115*a*, 115*b*, could differ (e.g., have different wavelengths, have different coherence lengths, be directed toward the environment from different angles, have different beam divergences) such that the beams of illumination 115*a*, 115*b* preferentially interact with elements of the biological tissue 105 (e.g., blood, blood cells, cells, fluids, connective tissue) within respective different ranges of depths 107, 109 within the biological tissue 105. For example, a different amount of attenuation of the beams of illumination by the biological tissue 105 (e.g., related to a wavelength-dependence of an attenuation coefficient of the biological tissue 105 or some other wavelength-dependence of an optical property of the biological tissue) could result in emitted light 125*a* and 125*b* received by the light sensor 120 in response to the illumination having interacted with (e.g., having been transmitted through, scattered by, refracted by, reflected from) elements of the biological tissue 105 within respective ranges of depths 107 and 109, respectively. In another example, the light sensor 120 could be configured to detect a time-varying pattern of constructive and destructive interference in the light 125*a*, 125*b* emitted from the biological tissue 105 in response to illumination by respective beams of illumination 115*a*, 115*b*. In such examples, the first 115*a* and second 115*b* beams of illumination could differ with respect to a coherence length. As a result, one or more properties (e.g., speckle rate, frequency content) of the time-varying patterns of constructive and destructive interference detected in the first 125*a* and second 125*b* emitted lights could be related to changes (e.g., the motion of blood cells, motion or deformation of the biological tissue 105) within respective different ranges of depths 107, 109 within the biological tissue 105 (e.g., due to a relationship between the coherence lengths of the first 115*a* and second 115*b* beams of illumination and an overall path length or distribution of path lengths of light composing the first 125*a* and second 125*b* emitted lights, respectively).

Figure 2A:
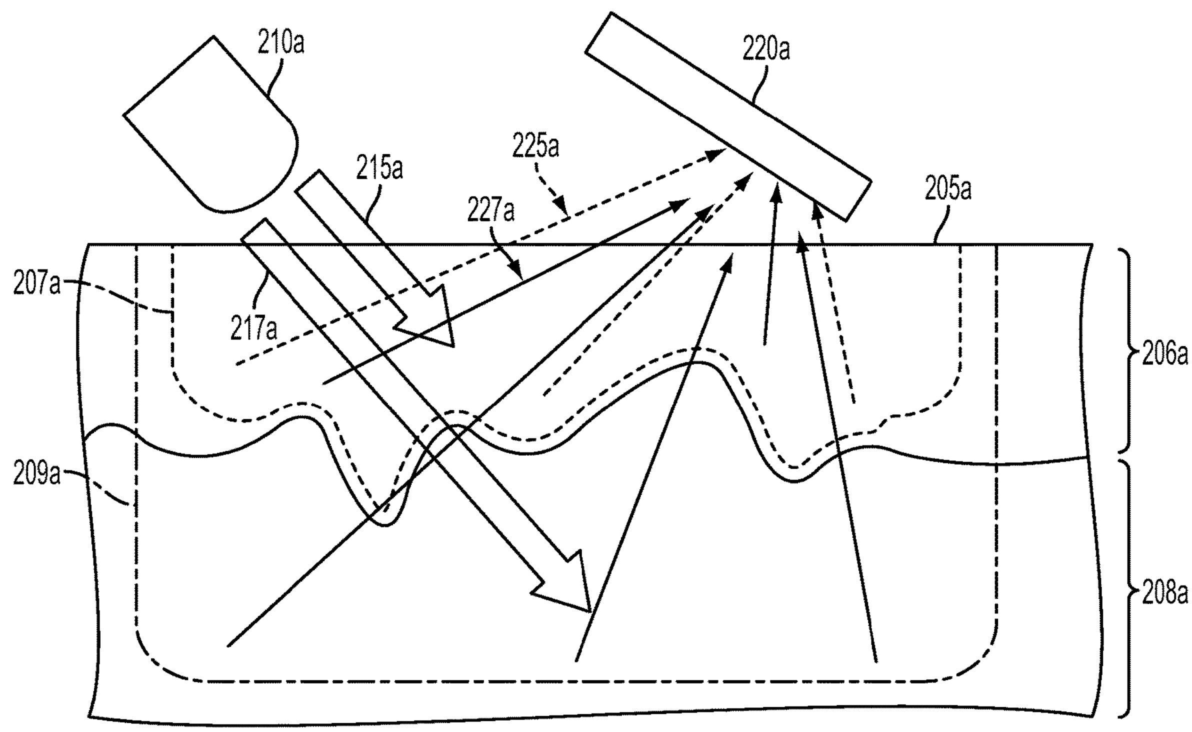
FIG. 2A is a side partial cross-sectional view of an example system, while measuring fluid flow in biological tissue.

Differences between first and second (or more) beams of illumination could result in the beams of illumination preferentially interacting with respective sets of elements, regions, or other partitions of an illuminated environment of interest that are separated, segregated, or otherwise distinct in other ways. For example, first and second beams of illumination could differ in one or more ways such that the beams of illumination preferentially interact with respective different types of tissue, different types of material, different layers of tissue or material, different cell types, different phases of a fluid or solid, or regions of an environment of interest that differ in some other way. FIG. 2A is a cross-sectional view through biological tissue 205*a* illustrating the operation of an example system 200*a* that includes a light source 210*a* configured to emit first 215*a* and second 217*a* beams of coherent illumination into the biological tissue 205*a*. The biological tissue 205*a* includes a surface layer 206*a* and a deep layer 208*a*. The first 215*a* and second 217*a* beams of illumination preferentially interact with respective first 207*a* and second 209*a* regions of the biological tissue 205*a* corresponding to the surface layer 206*a* and the deep layer 208*a*. The system 200*a* additionally includes a light sensor 220*a* configured to receive first 225*a* and second 227*b* light emitted from the biological tissue 205*a* in response to illumination by the first 215*a* and second 217*a* beams of illumination, respectively. The first 225*a* and second 227*a* emitted lights are emitted from respective first 207*a* and second 209*a* regions of the biological tissue 205*a*.

The first 215*a* and second 217*a* beams of illumination could differ in a variety of ways, related to a variety of properties of the surface layer 206*a* and the deep layer 208*a*, such that the first 215*a* and second 217*a* beams of illumination preferentially interact with the first 207*a* and second 209*a* regions, respectively. In some examples, the first 215*a* and second 217*a* beams of illumination could have respective first and second wavelengths, and an optical property of the deep layer 208*a* could be such that light at the first wavelength is absorbed by the deep layer 208*a* to a greater extent than light at the second wavelength is absorbed by the deep layer 208*a*. As a result, substantially all of the first emitted light 225*a* could be reflected, refracted, or otherwise affected by interaction with elements (e.g., cells) of the surface layer 206*a*. Conversely, the second emitted light 227*a* could include light reflected, refracted, or otherwise affected by interaction with elements (e.g., cells) of both the surface layer 206*a* and the deep layer 208*a*. In another example, the first 215*a* and second 217*a* beams of illumination could differ in coherence length and a property of scattering of light could differ between the surface layer 206*a* and the deep layer 208*a*.

Figure 2B:
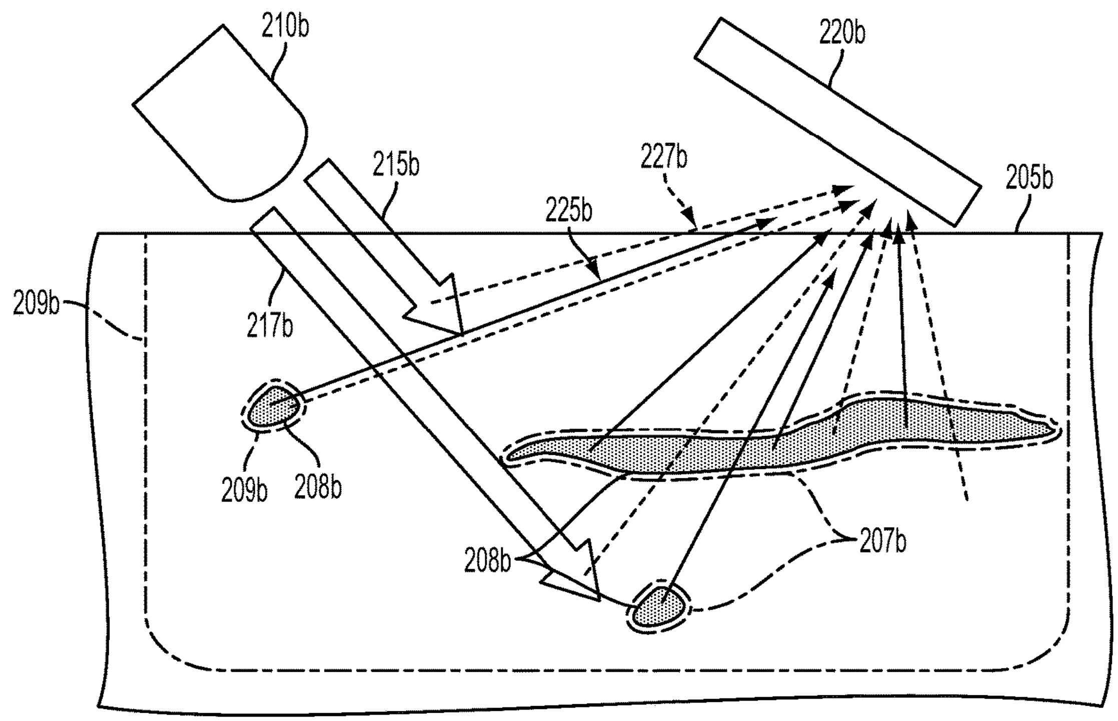
FIG. 2B is a side partial cross-sectional view of an example system, while measuring fluid flow in biological tissue.

Differences between first and second (or more) beams of illumination could result in the beams of illumination preferentially interacting with respective types of elements (e.g., blood cells, blood) that are distributed throughout and/or within an environment. For example, first and second beams of illumination could differ in one or more ways such that the first beam preferentially interacts with elements of interest (e.g., blood cells) distributed throughout an environment while the second beam interacts with alternative or additional elements within the environment (e.g., preferentially interacts with the remainder of the environment, preferentially interacts with the entirety of the environment including the blood cells). FIG. 2B is a cross-sectional view through biological tissue 205*b* illustrating the operation of an example system 200*b* that includes a light source 210*b* configured to emit first 215*b* and second 217*b* beams of coherent illumination into the biological tissue 205*b*. The biological tissue 205*b* includes portions of subsurface vasculature 208*b* that contain blood and blood cells. The first 215*b* and second 217*b* beams of illumination preferentially interact with respective first 207*b* and second 209*b* regions of the biological tissue 205*b* corresponding to the portions of subsurface vasculature 208*b* and the biological tissue 205*b* as a whole, respectively. The system 200*b* additionally includes a light sensor 220*b* configured to receive first 225*b* and second 227*b* light emitted from the biological tissue 205*b* in response to illumination by the first 215*b* and second 217*b* beams of illumination, respectively. The first 225*b* and second 227*b* emitted lights are emitted from respective first 207*b* and second 209*b* regions of the biological tissue 205*b*.

The first 215*b* and second 217*b* beams of illumination could differ in a variety of ways, related to a variety of properties of the portions of subsurface vasculature 208*b* and the biological tissue 205*b* as a whole, such that the first 215*b* and second 217*b* beams of illumination preferentially interact with the first 207*b* and second 209*b* regions, respectively. In some examples, the first 215*b* and second 217*b* beams of illumination could have respective first and second wavelengths, and an optical property of blood in the portions of subsurface vasculature 208*b* could be such that light at the second wavelength is differently (e.g., more) absorbed by the blood relative to the level of absorption of light at the second wavelength by the blood. As a result, differences in one or more properties of the first 225*b* and second 227*b* emitted lights (e.g., patterns of constructive and destructive interference, differences in wavelength relative to the wavelength of a corresponding beam of illumination) could be related to properties (e.g., a flow rate of blood, a distribution of velocities of blood cells) of the portions of subsurface vasculature 208*b* (e.g., due to the first 225*b* and second 227*b* emitted lights differing in their degree of interaction with portions of subsurface vasculature 208*b*).

Flow properties in an environment of interest (e.g., a biological tissue) could be determined by a variety of methods based on a variety of properties of light(s) emitted from the environment in response to illumination by one or more beams of coherent light that differ with respect to one or more properties. In some examples, properties of patterns of constructive and destructive interference in light emitted from the environment in response to coherent illumination can be related to properties of scattering elements (e.g., blood cells) in the environment (e.g., the location of scattering elements in the environment, refractive index of elements of the environment). Thus, time-dependent changes in the configuration of the environment (e.g., movement of scatterers in a fluid flow in the environment) could result in a time-dependent change in the patterns of constructive and destructive interference in the emitted light. As a result, such time-varying patterns of constructive and destructive interference in light emitted responsive to illumination by one or more beams of coherent light could be detected and used to determine flow properties in the environment.

FIGS. 3A-3E illustrate the operation of an example system 300 that could be operated to determine flow properties (e.g., flow rates within a volume) of blood in a portion of subsurface vasculature 307 and/or other portions of tissue in an arm 305. The system 300 includes a light source 310 configured to emit a beam of coherent illumination (a portion of which is illustrated as illumination 315) having one or more specified properties (e.g., wavelength, coherence length, beam divergence) into tissue of the arm 305 that includes the portion of subsurface vasculature 307 and blood cells (e.g., illustrative blood cell 309) contained in the portion of subsurface vasculature 307 that move along with blood in the portion of subsurface vasculature 307. The system 300 additionally includes a light sensor that includes an aperture 321 and a particular light-sensitive element 320 configured to detect a time-varying pattern of constructive and destructive interference in a portion of the beam of coherent illumination 315 that is scattered by tissue of the arm 305 and that is emitted as an emitted light 321 toward the light sensor such that the emitted light 321 is received by the particular light-sensitive element 320.

Note that the system shown could be adapted to emit multiple beams of illumination (e.g., 315) differing with respect to one or more properties and to receive respective different lights emitted from the arm 305 responsive to illumination by such multiple beams simultaneously (e.g., using multiple respective lasers and/or multiple respective light-sensitive elements of the light sensor) or during respective different periods of time (e.g., using a single light source configured to emits beams of light having different specified properties during different period of time). Further, the light sensor shown is configured to detect a single time-varying pattern of constructive and destructive interference in light received from a particular region of the arm 305, but such a light sensor could include further light-sensitive elements configured to detect further time-varying patterns of constructive and destructive interference in light received from further particular portions of the arm (e.g., the light sensor could be a camera) and/or to detect other properties (e.g., a wavelength, spectrographic information) of such received light.

Figure 3A:
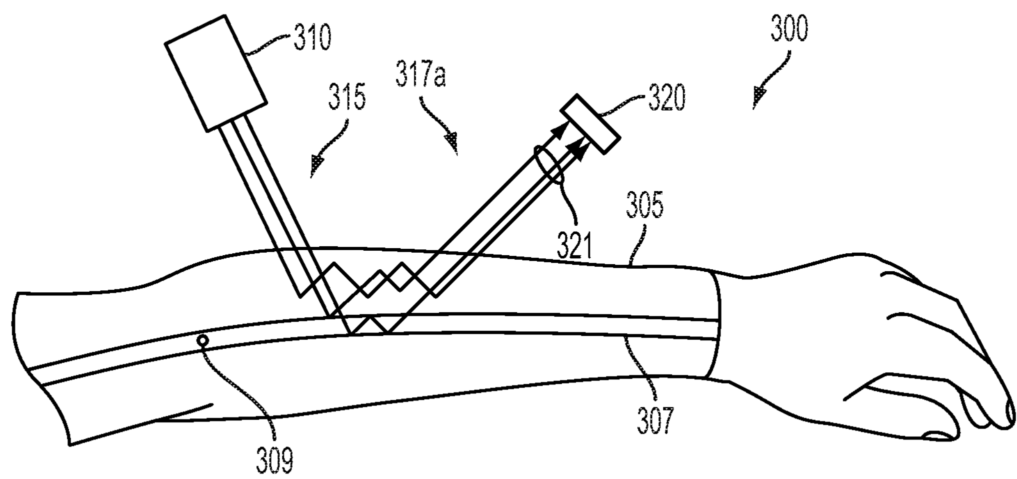
FIG. 3A is side partial cross-sectional view of an example system, while measuring blood flow in a human arm.
Figure 3B:
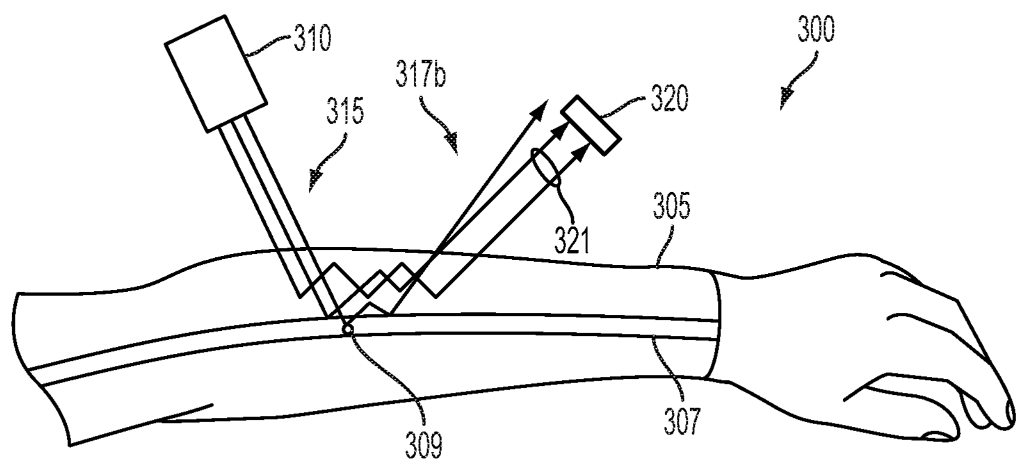
FIG. 3B is side partial cross-sectional view of the example system illustrated in FIG. 3A, while measuring blood flow in a human arm.
Figure 3C:
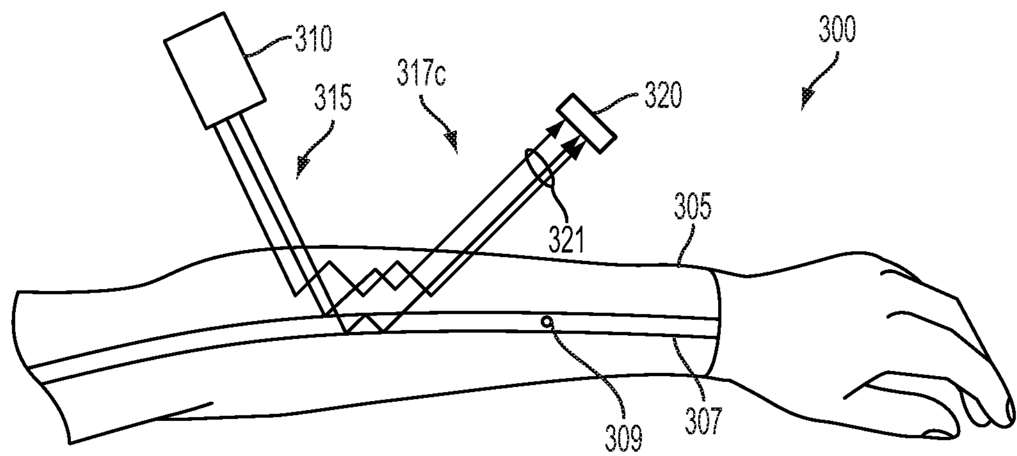
FIG. 3C is side partial cross-sectional view of the example system illustrated in FIG. 3A, while measuring blood flow in a human arm.
Figure 3D:
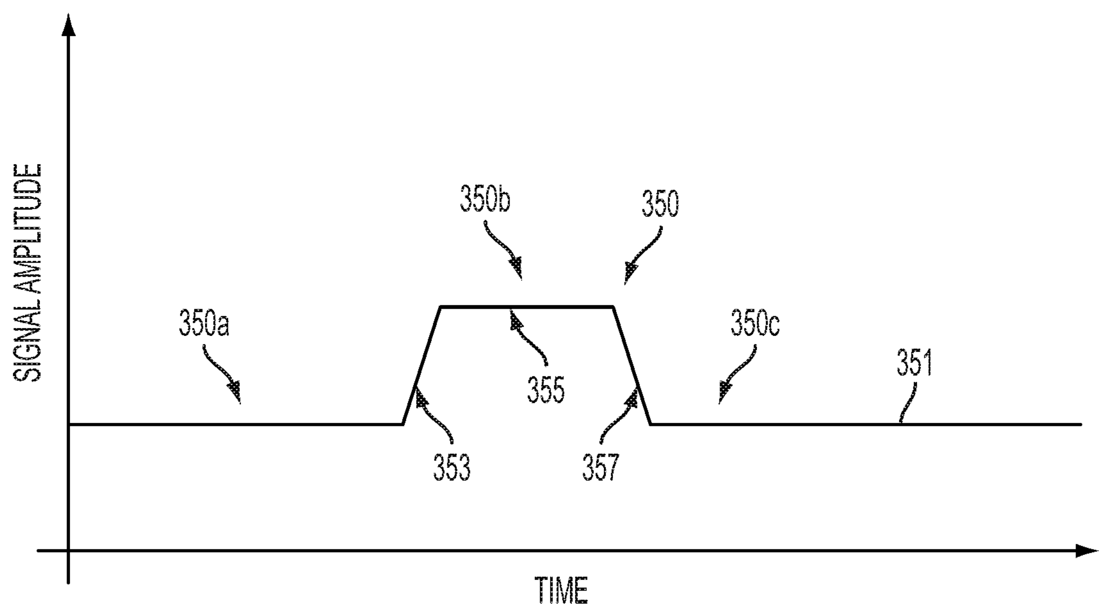
FIG. 3D is an example output generated by the example system illustrated in FIGS. 3A-3C.

To illustrate the operation of the system 300, the movement of an illustrative blood cell 309 due to blood flow in the portion of subsurface vasculature 307 is illustrated in FIGS. 3A-3C and the corresponding time-dependent changes of the pattern of constructive and destructive interference detected by the particular light-sensitive element 320. Specifically, FIG. 3D illustrates an example detected light intensity waveform 351 corresponding to the intensity of the time-varying pattern of constructive and destructive interference in light emitted from a particular portion of the arm 305 as detected by the particular light-sensitive element 320.

FIG. 3A illustrates the system 330 and arm 307 during a first period of time. The illustrative blood cell 309 is in an upstream region of the portion of subsurface vasculature 307 that is substantially outside of a region illuminated by the illustrated coherent illumination 315. As a result, the particular light-sensitive element 320 detects a first light intensity 350*a* related to a pattern of constructive and destructive interference in first emitted light 317*a*.

FIG. 3B illustrates the system 330 and arm 307 during a second period of time. The illustrative blood cell 309 is moved downstream due to blood flow into the region of the portion of subsurface vasculature 307 that is illuminated by the illustrated coherent illumination 315 and thus acts to scatter the illustrated coherent illumination 315. As a result, the particular light-sensitive element 320 detects a second light intensity 350*b* related to a pattern of constructive and destructive interference in second emitted light 317*b* that is substantially different from the pattern of constructive and destructive interference in first emitted light 317*a*.

FIG. 3C illustrates the system 330 and arm 307 during a third period of time. The illustrative blood cell 309 is moved downstream due to blood flow into a downstream region of the portion of subsurface vasculature 307 that is substantially outside of the region illuminated by the illustrated coherent illumination 315. As a result, the particular light-sensitive element 320 detects a third light intensity 350*c* related to a pattern of constructive and destructive interference in third emitted light 317*c* that is substantially similar to the pattern of constructive and destructive interference in first emitted light 317*a*.

The movement of the illustrative blood cell 309 through the portion of subsurface vasculature 305 during and between the first, second, and third periods of time (as illustrated in FIGS. 3A-C, respectively) results in the particular light-sensitive element 320 detecting an illustrative speckle event 350 in the detected light intensity waveform 351. The illustrative speckle event 350 is a trapezoidal pulse that includes a rising edge 353, a plateau 355, and a falling edge 357. One or more of these waveform elements could be related to the speed of the illustrative blood cell 309 and thus to a flow property in the biological tissues of the arm 305 (e.g., of the blood in the portion of subsurface vasculature 307). In some examples, a time property (e.g., a rise time of the rising edge 353, a duration of the plateau 355, a fall time of the falling edge 357) of the speckle event 350 could be related to a speed of the illustrative blood cell 309. For example, the rate of increase in intensity during the rising edge 353 could correspond to the velocity of the illustrative blood cell 309 such that higher rates correspond to higher velocities.

Note that the movement of the illustrative blood cell 309 and the corresponding detected light intensity waveform 351 are meant as illustrative examples. A portion of subsurface vasculature could include many blood cells having respective different velocities related to the movement of blood in the portion of subsurface vasculature. Further, the movement of an individual blood cell through a region of subsurface vasculature illuminated by a coherent light source could result in no speckle event, multiple speckle events, or some other feature(s) to be present in a detected light intensity waveform or other detected signal related to the pattern of constructive and destructive interference in a portion of a beam of coherent illumination that is scattered the environment including the portion of subsurface vasculature and blood cell(s) and that is emitted as an emitted light toward a light sensor.

Figure 3E:
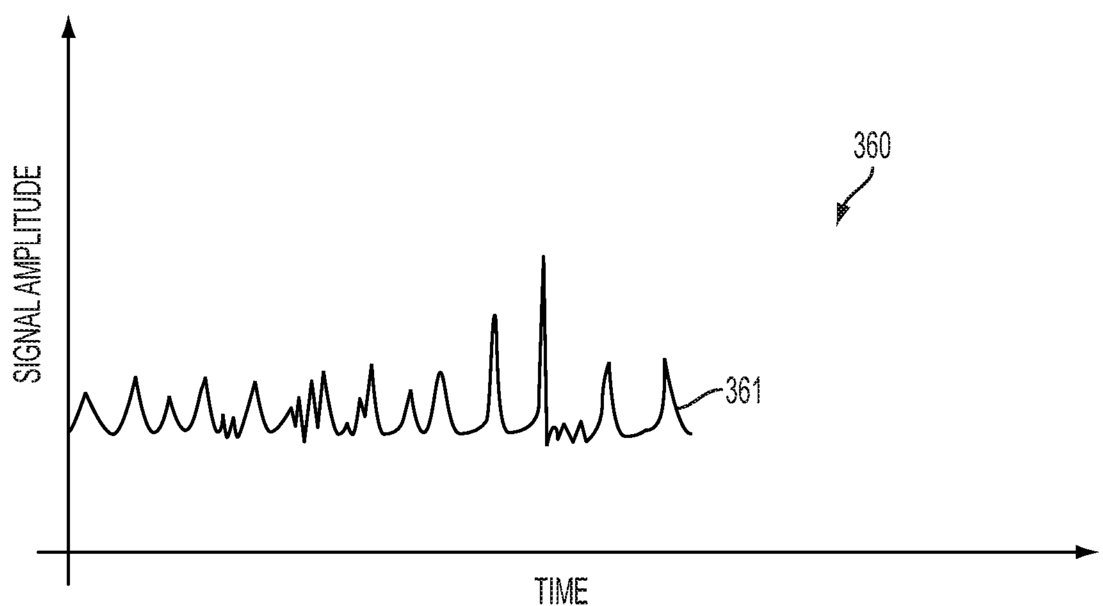
FIG. 3E is an example output generated by the example system illustrated in FIGS. 3A-3C.

FIG. 3E shows an example detected light intensity waveform 361 that could be detected using the system 300 when a plurality of blood cells and other scatterers are being moved in a flow of blood or other fluids in the arm 305. The detected light intensity waveform 361 includes a plurality of speckle events having respective shapes, durations, amplitudes, rise/fall times, and/or other properties. The system 300 could include electronics (e.g., amplifiers, filters, comparators, envelope detectors, slope detectors, differentiators, peak detectors, ADCs, microprocessors, microcontrollers) configured to determine one or more flow properties in biological tissue of the arm 305 (e.g., of the blood in the portion of subsurface vasculature 307) based on the detected light intensity waveform 361. For example, the electronics could be configured to detect a rise time of individual speckle events in the detected light intensity waveform 361 and to determine a corresponding blood cell velocity. The electronics could be further configured to determine a distribution of velocities of individual blood cells in the blood or other fluid, a mean flow rate of the blood or other fluid, and/or some other flow property of the blood or other fluid in the biological tissues of the arm 305.

In some examples, spectrographic properties (e.g., a wavelength, a line width, a spectrum, a center frequency, a width, a shape, or some other property of a peak or other feature of a spectrum) of light emitted from the environment in response to coherent illumination can be related to properties of scattering elements (e.g., blood cells) in the environment (e.g., the velocity of scattering elements in the environment, motion of the environment relative to a source of illumination and/or a light sensor). Thus, the configuration of the environment (e.g., a distribution of velocities of scatterers in a fluid flow in the environment) could be detected to determine flow properties in the environment. For example, scattering of illumination by a moving scatterer (e.g., a blood cell moving in a blood flow) could cause the wavelength of the illumination to change by an amount related to the velocity of the scatterer, the angle between the direction of the illumination and the velocity of the scatterer, the angle between the velocity of the scatterer and the angle into which the illumination is scattered, and the wavelength of the illumination. As a result, such scattered, wavelength-shifted light could form a part of the light emitted from the environment and detected by a detector, and flow properties in the environment (e.g., related to the motion of such scatterers in a fluid flow) could be determined based on detected spectrographic properties of the emitted light.

Received emitted light from the environment could include light at wavelengths that have a difference relative to the wavelength of illumination used to illuminate the environment. Such a difference could be detected (e.g., using a spectrometer, using an interferometer, using a plurality of light-sensitive elements sensitive to light within respective different ranges of wavelengths) and used to determine a flow property in the environment (e.g., to determine a flow rate of a fluid that contains the scatterers that scattered the illumination out of the environment as the emitted light). Additionally or alternatively, a spectral profile, a line width, a degree of spectral spreading relative to the beam of coherent illumination, or some other spectrographic properties of the emitted light could be detected and used to determine flow properties in the environment (alone or on combination with properties of received light emitted from the environment in response to illumination by additional beams of illumination). Further, such detected properties of the emitted light could be used to determine an overall motion and/or deformation of the environment (e.g., motion or deformation of tissue containing blood cells) relative to a light source, light sensor, and/or some other components configured to detect flow properties in the environment.

Determined flow properties in an environment (e.g., of blood at one or more points within a portion of subsurface vasculature and/or at other locations in a biological tissue) could be any properties or physical parameters relating to a flow of a fluid within the environment. In some examples, determined flow properties could include the velocity, direction, acceleration, or other information about the movement of individual particles (e.g., blood cells or other scatterers) or groups of particles within the environment. For example, a system could determine the velocity of individual particles in the environment based on a detected temporal property of speckle events in one or more time-varying patterns of constructive and destructive interference, a detected difference in wavelength relative to a beam of illumination, or some other features of a received light emitted by the environment in response to illumination by two or more different beams of coherent light. In some examples, determined flow properties could include properties describing a bulk flow of fluid, e.g., a flow rate, a mean flow velocity, a mean flow speed, a mass flow rate, or some other property of a fluid flow in an environment.

In some examples, the detected flow properties could correspond to respective portions (e.g., sub-regions, voxels, elements) of an environment, e.g., blood cells in a particular volume of biological tissue (e.g., a portion of vasculature, a portion of a vein, a portion of an artery, a portion of a capillary bed) or other portion of anatomy. The location of the specified region could be related to the specified properties of the beams of illumination used to illuminate the environment. For example, first and second beams of illumination could have properties specified such that the first and second beams of illumination preferentially interact with elements of the environment within respective different ranges of depths. In such an example, a flow property could be determined, based on received lights emitted from the environment in response to respective beams of illumination, in a portion of the environment at a depth corresponding to preferential interaction with a particular one of the beams of illumination, or corresponding to preferential interaction with both of the beams of illumination.

A light source (e.g., 110, 210*a*, 210*b*, 310) as described herein could be configured in a variety of ways and include a variety of elements such that emitted beams of coherent illumination (e.g., 115*a*, 115*b*) differ in one or more specified properties according to an application. The beams of coherent illumination could have specified different wavelengths. In some examples, the wavelengths of one or more beams of coherent illumination could be specified such that they could penetrate an environment of interest, be scattered by scatterers in a fluid flow(s) in the environment of interest, or according to some other considerations. For example, the environment could include portions of vasculature within a portion of human anatomy (e.g., within a portion of tissue targeted for a surgical intervention, within a wrist), the determined flow properties could be flow properties of blood at a plurality of locations within the portion of human anatomy, and the wavelength(s) of the beam(s) of coherent illumination could be between approximately 400 nanometers and approximately 1000 nanometers. In some examples, the wavelengths of the beam(s) of coherent illumination could be specified relative to a characteristic size or other property of scatterers (e.g., blood cells, cavitation bubbles, natural and/or artificial particles, bubbles or gas or other material having dissimilar optical properties to a surrounding fluid medium) such that the scatterers could scatter the beam(s) of coherent illumination and cause the environment to emit light having time-varying patterns of constructive and destructive interference or other properties (e.g., differences in wavelength relative to the beam(s) of illumination) related to the configuration of the environment and/or scatterers (e.g., related to motion of the scatterers within fluid flows in an environment). The wavelength(s) of the beam(s) of coherent illumination could be within a near-infrared (NIR) transparency window of biological tissue (e.g., between approximately 650 and approximately 950 nanometers and/or between approximately 1000 and approximately 1350 nanometers). In some examples, the wavelengths of two (or more) beams of illumination could differ such that the beams of illumination preferentially interact with respective different sets of elements and/or regions of the environment (e.g., overlapping sets of elements and/or regions).

In some examples, the beams of coherent illumination could have coherence lengths that are greater than some minimum coherence length (e.g., greater than 1 millimeter) that is related to scattering properties of elements of the environment (e.g., skin cells, connective tissue, portions of subsurface vasculature, blood cells, and other elements of biological tissues of a portion of human anatomy). The specified minimum coherence length could be related to a spacing of scatterers or other optical features (e.g., reflecting, refracting, and/or diffracting interfaces between regions having different indices of refraction, metallic and/or semiconductive elements) in the environment such that one or more properties of time-varying patterns of constructive and destructive interference or other properties of the scattered light can be detected and used to determine flow properties in the environment. Additionally or alternatively, the specified minimum coherence length could be related to a range of expected path lengths of scattered light through the environment. Further, light sources (e.g., 110, 210*a*, 210*b*, 310) configured to emit such beams of illumination could include a volume holographic grating, a monochromator, a Lyot filter, a Bragg reflector, a dielectric mirror, or some other element(s) configured to increase a coherence length of and/or decrease a spectral linewidth of the beam of coherent illumination. Such elements could be disposed on a discrete laser (e.g., a volume holographic grating could be disposed in the path of the beam of a laser) and/or could be incorporated into one or more elements of the light source (e.g., mirrors, lenses, gain media, frequency doublers, or other elements of the light source could be configured such that they had properties of one or more of the listed additional elements). In some examples, the coherence lengths of two (or more) beams of illumination could differ such that the beams of illumination preferentially interact with respective different sets of elements and/or regions of the environment (e.g., elements and/or regions within different respective ranges of depths in the environment).

The light source (e.g., 110, 210_a_, 210_b_, 310) could include one or more lasers selected from a wide variety of lasers according to an application. The laser(s) could include a gas laser, a chemical laser, a dye laser, a metal-vapor laser, a solid-state laser, a semiconductor laser, or any other type of laser configured to produce a beam of coherent illumination having one or more specified properties (e.g., wavelength, spectral line width, coherence length, beam width, beam dispersion) such that the laser could illuminate an environment of interest (e.g., a portion of subsurface vasculature, tissues undergoing a surgical intervention) that contains light-scattering elements (e.g., blood cells, human tissue) such that the environment of interest responsively emits light having one or more properties that can be detected and used to determine flow properties (e.g., a flow rate of blood within a particular portion) in the environment. In some applications the laser(s) could be configured to satisfy limited power and space requirements such that a system including it could be battery-powered and could be comfortably worn by a wearer (e.g., worn around a wrist of the wearer).

In some examples, the laser(s) could be a small laser diode, e.g., a VCSEL, a double heterostructure laser, a quantum well laser, or some other structure of semiconductor laser incorporating gallium nitride, indium gallium nitride, aluminum gallium indium phosphide, aluminum gallium arsenide, indium gallium arsenide phosphide, lead salt, or some other material or combination of materials as a gain medium. In some examples, the laser(s) could include frequency doublers, optics, collimators, or some other elements according to an application. Further, the laser(s) could be configured to control the direction of emitted beam(s) of coherent illumination (e.g., by including servos, motors, piezo elements, or other actuators configured to translate and/or rotate the laser(s) and/or optics or other elements thereof) to enable detection of flow properties in specified sub-regions of an environment of interest by directing the beam(s) of coherent illumination toward the different specified sub-regions of the environment.

In some examples, the light source (e.g., 110, 210_a_, 210_b_, 310) could include two or more lasers configured to emit respective two or more beams of coherent illumination differing with respect to one or more properties (e.g., wavelength, coherence length, beam divergence). In some examples, the light source could include a single laser configured to emit two or more beams of coherent illumination that differ with respect to one or more properties during respective different periods of time. For example, such a laser could be a tunable laser such that one or more properties (e.g., a cavity length, a gain medium refractive index, a reflectivity spectrum of a mirror) of the laser are controllable to control the wavelength of coherent illumination emitted by the laser. In another example, the laser could be configured to emit beams of coherent illumination having a controllable coherence length. This could include the laser being configured to detune a cavity of the laser to decrease the coherence length of the illumination emitted by the laser by, e.g., controlling a cavity length or a gain medium refractive index. The laser could be a tunable laser (i.e., able to be operated to control a wavelength of the illumination output by the laser) and the coherence length of the illumination emitted by the laser could be decreased by changing the controlled wavelength of the laser around a specified wavelength at a high frequency. Additionally or alternatively, the coherence length of the laser could be controlled by injecting a carrier beam of illumination into the laser, by modulating the output of the carrier at a high frequency, or by some other method.

In some examples, the light source (e.g., 110, 210_a_, 210_b_, 310) could include more than one laser. Individual lasers of the more than one laser could have respective specified properties (e.g., wavelengths, line widths, spectral profiles, coherence lengths, beam divergences) according to an application. More than one light source could be provided to allow for detection of a flow properties in more than one region of an environment. In some embodiments, a spatially distributed array of light sources could be provided such that individual light sources of the array emit respective beams of coherent illumination into respective individual sub-regions (e.g., overlapping or non-overlapping portions of tissue) of an environment of interest. Such an array of lasers could be operated to determine the flow properties of the respective individual sub-regions of the environment (e.g., to determine a flow map within the environment, to determine a location, shape or other property of vasculature in a biological tissue, or according to some other application).

A light sensor (e.g., 120, 220_a_, 220_b_) as described herein could be configured in a variety of ways and include a variety of light-detecting apparatus configured to detect properties of light that is emitted by an environment in response to illuviation by beams of coherent illumination that are related to the configuration of the environment and/or scatterers therein. The light sensor could include one or more photodetectors, photodiodes, phototransistors, CCDs, active pixel sensors, angle-sensitive pixels, photoresistors, or other light-sensitive elements. Such light-sensitive elements and/or other light-sensitive elements of the light sensor could be configured to detect an intensity, a wavelength, a spectrum, a degree of polarization, a direction of polarization, or some other property of light emitted by the environment. In some examples, the light sensor could comprise a camera (i.e., including, e.g., an aperture 321, a plurality of particular light-sensitive elements 320, and/or optics). In some examples, the light sensor could include a spectrometer configured to detect a wavelength or other spectrographic information (e.g., a spectral profile, a center frequency, a width, a shape, or some other property of a peak or other feature of a spectrum) of received light emitted from the environment (e.g., the light sensor could include a plurality of light-sensitive elements disposed relative to an optically dispersive element, e.g., a diffraction grating, a prism, such that individual light-sensitive elements receive detect the intensity of the received light within respective ranges of wavelengths). In some examples, the light sensor could include an interferometer or other component(s) configured to determine a difference between a wavelength of light received from the environment and a reference wavelength, e.g., a reference wavelength of a beam of illumination used to illuminate the environment and in response to which the received light is emitted from the environment.

The light sensor (e.g., 120, 220_a_, 220_b_) and/or light-sensitive elements thereof (e.g., 320) could include a variety of components according to an application. The imager could include lenses, polarization filters, color filters, apertures, mirrors, diffraction gratings, liquid crystal elements, baffles, or other optical elements to affect the light received by the imager and/or by particular light-sensitive elements thereof. In some examples, the imager could include a color filter configured to substantially block light having wavelengths different from a wavelength of one or more beams of illumination (e.g., 115*a*, 115*b*) emitted by a light source (e.g., 110, 210*a*, 210*b*).

Note that the example speckle event 350 and other features of the example detected light intensity waveform 361 illustrated in FIGS. 3D and 3E, respectively, are meant as illustrative examples of signals related to time-varying patterns of constructive and destructive interference in light emitted from an environment of interest that could be used to determine flow properties in the environment. Rise times, rise rates, pulse widths, fall times, fall rates, and other temporal features of such detected signals are non-limiting examples of time-dependent waveform features that could be used to determine flow properties in an environment. Additionally or alternatively, an envelope, a spectrum, a derivative, a power in one or more frequency bands, a speckle or other event rate, an autocorrelation, or some other variable or variables related to such detected signals could be used to determine flow properties in an environment.

Note that the detection of flow properties in biological tissues 105, 205*a*, 205*b*, 305 (e.g., in blood in a portion of subsurface vasculature 307 of an arm 305) based on properties of light emitted from the biological tissues in response to illumination by two or more beams of coherent light that differ with respect to one or more properties are intended as non-limiting illustrative examples of the detection of flow properties in environments that scatter light and that include scatterers that have time-dependent properties (e.g., location, orientation) related to flow in the environment by illuminating such environments with two or more beams of coherent illumination differing with respect to one or more properties. For example, the environment could be any tissue of a human (e.g., an ankle, an ear, a neck, a portion of central vasculature, a tumor, a tissue undergoing a surgical intervention and/or exposed during such an intervention) or animal, and the flow properties could be a property of flow in any fluid of the human or animal body (e.g., arterial blood, capillary blood, venous blood, lymph, interstitial fluid, stomach or other digestive contents, air in the airways and/or lungs, cerebrospinal fluid). The environment could be an in vivo biological environment (e.g., a tissue of a living human, animal, plant, etc.) or an in vitro environment. The environment could be a biological sample in a sample container, cuvette, pipette, microscope slide, or other vessel. The environment could be part of a biological or chemical process. For example, the environment could be a fluid in a water treatment process, a fluid in a food or drug preparation process, a lake, stream, or river in a natural environment, or some other environment. In another example, the fluid could be a fluid of a microfluidic assay or other microfluidic device or assembly. The environment could be a liquid, a gel, a solid, or some other phase of matter or combination of phases (e.g., an emulsion). The environment could include biological samples that had been freeze-dried, desiccated, frozen, vaporized, alkalated, or otherwise prepared, including adding the imaging agent (i.e., functionalized nanodiamonds and functionalized magnetic particles) to the environment.

In some examples, systems and methods as described herein could be applied to determine flow properties in biological tissues that are subject to a surgical intervention. That is, flow properties could be determined in a portion of biological tissue that has been exposed during a surgical intervention, that contains a target to be ablated, excised, resected, or otherwise manipulated (e.g., that contains a tumor, cyst, epileptic center, or infectious agent), that contains a biological structure to be modified (e.g., an aneurysm to be repaired, a vascular anastomosis to be cauterized, a re-entrant conductive cardiac fiber to be severed), that contains a portion of sensitive tissue (e.g., a portion of eloquent cerebral cortex). In such examples, methods and systems as described herein could be applied to determine flows in such biological tissue in order to, e.g., determine a level of perfusion within and/or across the tissue, to determine the location, pattern, width, depth, or other information about vasculature in such a biological tissue, to detect the location of a tumor or other target structure and/or tissue in the biological tissue, or to determine some other information about the biological tissue.

Such determined information could be used to ablate a target (e.g., a tumor whose location has been determined), to avoid damaging a sensitive tissue (e.g., to avoid mechanical or thermal damage to a tissue, to avoid disrupting perfusion of and/or vascular supply to the tissue), to determine a portion a vasculature through which to introduce a drug or other substance, to determine a portion a vasculature from which to extract a blood or other tissue sample, or to accomplish and/or instruct some other application(s). Such determined information could be presented to a human surgeon (e.g., via a heads-up-display, via a control console of a robotic surgical system) to inform the performance of a surgical intervention by the surgeon and/or used to determine the operation of a robotic surgical system (e.g., to automatically or semi-automatically ablate a target tissue at a determined location while avoiding damaging sensitive tissues by, e.g., avoiding inflicting damage to vasculature perfusing such sensitive tissue).

Scatterers in the environment could be discrete particles (e.g., blood cells, other cells, micelles, vacuoles, immiscible globules (e.g., oil globules in water), engineered particles (e.g., quantum dots, PEG particles, microparticles of a conductive, semiconductive, magnetic, or other material)) in the environment, or could be discontinuities within the fluid whose flow is being determined (e.g., cavitation bubbles, localized turbulence, high thermal and/or pressure gradients, shock waves). The scatterers could be present in the environment (e.g., cells in blood or other biological fluids, microorganisms, particles of silt, or other scatterers in an environmental fluid (e.g., a stream, a pond)) or could be introduced (e.g., production of cavitation bubbles by application of directed energy and/or mechanical intervention, injection of scattering particles (e.g., functionalized particles) into the bloodstream of a human or animal).

Scatterers in an environment could have one or more properties that can be detected and that are related to one or more properties of the environment. For example, a scatterer could selectively interact with an analyte of interest (e.g., the scatterer could be functionalized with a bioreceptor specific to the analyte) and a drag coefficient or other property of the scatterer could be related to the scatterer binding to the analyte. Thus, detection of the velocity of such an individual scatterer or population of such scatterers, relative to one or more determined and/or detected flow properties of the environment containing the scatterer(s), could enable determination of one or more properties of the analyte (e.g., a concentration of the analyte). Further, a motion and/or deformation of the environment containing such scatterers could be detected using the systems and methods described herein. Further such detected motions and/or deformations could be used to refine a determination of flow properties in the environment, e.g., to reduce a determined velocity of scatterers in a fluid flow by an amount corresponding to the velocity of a portion of the environment containing such scatterers.

Those of skill in the art will understand the term "scatterer" in its broadest sense and that it may take the form of any natural or fabricated material, a cell, a protein or aggregate of proteins, a molecule, cryptophan, a virus, a micelle, a phage, a nanodiamond, a nanorod, a quantum dot, a single-magnetic-domain crystal of a metal, etc. that can interact with light incident on the scatterer to reflect, refract, diffract, or otherwise scatter the incident light. Scatterers could be naturally present in an environment of interest (e.g., blood cells in a portion of subsurface vasculature) or could be added to the environment of interest. Further, a scatterer may be of any shape, for example, spheres, rods, non-symmetrical shapes, etc., and may be made of a solid, liquid or gaseous material or combinations thereof.

III. Example Determination of Flow Properties in Biological Tissue

Systems and methods described herein relate to the detection and/or determination of flow properties in biological tissues and other environments containing scattering elements by illuminating the biological tissue with first and second (or more) beams of coherent illumination that differ with respect to one or more properties and detecting one or more properties (e.g., time-varying patterns of constructive and destructive interference, a difference in wavelength relative to a wavelength of a corresponding beam of illumination) of respective first and second (or more) lights responsively emitted from the biological tissue in response to the illumination. A variety of flow properties (e.g., flow rates, flow directions, velocity distributions of scattering elements in fluid flows) could be detected at a plurality of points on and/or within the biological tissue. For example, the plurality of flow properties could include a plurality of flow rates of blood cells in the biological tissue (e.g., in blood within arteries, veins, or other vasculature in the tissue, in interstitial fluid of the tissue, in some other fluid flow in the tissue). Further, detection of properties of responsively emitted light(s) could include detecting an intensity, an amplitude, a polarization, a wavelength, a spectral content, a spectral profile, a center frequency, a width, a shape, or some other property of a peak or other feature of a spectrum of the light at one or more points in time and/or patterns of change over time of such properties using a variety of methods.

In some examples, first and second beams of coherent illumination could preferentially interact with respective first and second sets of elements of an environment of interest. Such sets of elements could comprise particular types of elements in the environment (e.g., cell types, tissue types, phases of matter, fluorophores, chemicals, minerals), elements within particular regions of the environment (e.g., within ranges of depths or other specified geometry on or within the environment, within layers of tissue or other materials in the environment), or could comprise some other overlapping, partially overlapping, or substantially disjoint partitioning of elements and/or regions of the environment. In some examples, the first and second sets of elements could contain a set of elements in common and the first and second beams of coherent illumination preferentially interacting with the in-common elements could include interacting with the in-common elements in respective different ways (e.g., scattering at different angles, scattering with different probabilities).

Illuminating an environment of interest with multiple beams of coherent light that differ in one or more properties and detecting responsively emitted lights from the environment could allow the determination of flow properties in particular region(s) of the environment, of particular element(s) of the environment, to a greater accuracy and/or specificity, or according to some other application relative to such determinations made based on the illumination of the environment with a single beam of coherent illumination. For example, a first emitted light received from the environment in response to illumination by a first beam of illumination could include a signal (e.g., a time-varying pattern of constructive and destructive interference, an intensity, a wavelength, a spectrum) of interest (e.g., a signal related to a flow property in a target portion of the environment with which the first beam of illumination preferentially interacts) and an unwanted signal (e.g., a noise signal, a signal related to a flow property in a non-target portion of the environment with which the first beam of illumination preferentially interacts, a signal related to a motion or deformation of the environment and/or of the target portion of the environment). A second emitted light received from the environment in response to illumination by a second beam of illumination could include a signal correlated to the unwanted signal such that the second emitted light could be detected and used, in combination with the detected first emitted light, to determine the signal of interest and/or to determine a flow property in the environment related to the signal of interest.

As an illustrative example, FIG. 4A shows first 410*a* and second 420*a* frequency content of a detected intensity of first and second lights, respectively, that are emitted from an environment of interest responsive to illumination of the environment by first and second beams of coherent illumination, respectively, that differ with respect to one or more properties (e.g., wavelength, coherence length, beam divergence). In some examples, information contained in the first 410*a* and second 420*a* frequency content could be related to flow properties in respective first and second sets of elements of the environment (e.g., elements within respective ranges of depths within the environment, elements of respective types of tissue and/or cells in the environment) with which the first and second beams of coherent illumination, respectively, preferentially interact. For example, a center frequency of one or more peaks in the frequency content could correspond to a speed of scattering elements (e.g., blood cells) in the environment. As illustrated, first frequency content 410*a* includes first and second peaks that could correspond to a first signal (e.g., a background amount of scattering of light in the tissue, a motion of the environment of interest relative to a light source and/or light sensor configured to generate the illustrated frequency content, a speed of blood cells within a first range of depths within the environment, a speed of non-blood scattering elements within the environment) and a second signal (e.g., a speed of blood cells within a second range of depths within the environment), respectively. The second frequency content 420*a* includes a first peak corresponding to the first peak of the first frequency content 410*a* and further corresponding to substantially the same first signal as the first peak of the first frequency content 410*a*.

The first signal could be determined based on information contained in the first peak of the second frequency content 420*a* (illustrated for comparison in FIG. 4B as first determined frequency content 430*a*). For example, the first signal could be related to a flow property within a range of depths of interest in the biological tissue. Alternatively, the first signal could be related to relative motion of the environment or some other baseline or offset signal, and could be used to determine such a baseline of offset signal such that the determined baseline or offset signal could be used to correct some other determined flow rate. The second signal could be determined based on information contained in the second peak. For example, the second signal could be determined and/or extracted from the first frequency content 410*a* by subtracting or otherwise removing the second frequency content 420*a* from the first frequency content 410*a* (illustrated in FIG. 4B as second determined frequency content 440*a*). One or more flow properties within a range of depths of interest in the biological tissue could be determined based on information contained in the determined and/or extracted second peak (e.g., form 440*a*). Additionally or alternatively, such flow properties could be offset, corrected, normalized, or otherwise adjusted based on some other flow property or other information determined from one or more lights received from the environment (e.g., based on an offset flow property determined from the first peak of the second frequency content 420*a*).

As another illustrative example, FIG. 4C shows first 410*c* and second 420*c* spectrographic content (e.g., intensities of a particular light as a function of wavelength of the particular light) of detected first and second lights, respectively, that are emitted from an environment of interest responsive to illumination of the environment by first and second beams of coherent illumination, respectively, that differ with respect to one or more properties (e.g., wavelength, coherence length, beam divergence). In some examples, information contained in the first 410*c* and second 420*c* spectrographic content could be related to flow properties in respective first and second sets of elements of the environment (e.g., elements within respective ranges of depths within the environment, elements of respective types of tissue and/or cells in the environment) with which the first and second beams of coherent illumination, respectively, preferentially interact. For example, a center wavelength of one or more peaks in the spectrographic content could correspond to a speed of scattering elements (e.g., blood cells) in the environment. As illustrated, second spectrographic content 420*c* includes first and second peaks (center wavelengths indicated by 707*c* and 409*c*, respectively) that could correspond to a first signal (e.g., a background amount of scattering of light in the tissue, a motion of the environment of interest relative to a light source and/or light sensor configured to generate the illustrated spectrographic content, a speed of blood cells within a first range of depths within the environment, a speed of non-blood scattering elements within the environment) and a second signal (e.g., a speed of blood cells within a second range of depths within the environment), respectively. The first spectrographic content 410*c* includes a first peak corresponding to the first peak of the second spectrographic content 420*c* and further corresponding to substantially the same first signal as the first peak of the second spectrographic content 420*c*.

The first signal could represent a wavelength offset of the first 410*c* and second 420*c* spectrographic content. For example, the first signal could be related to relative motion of the environment or some other baseline or offset signal, and could be used to determine such a baseline of offset signal such that the determined baseline or offset signal could be used to correct some other detected spectrographic content or other detected or determined information. This information could be used to offset, correct, normalize, or otherwise adjust the first 410*c* and/or second 420*c* spectrographic content. The center wavelength 407*c* (or some other property) of the first peak could be determined and/or extracted from the first spectrographic content 410*c* and used to offset, correct, normalize, or otherwise adjust the second spectrographic content 420*c*. This is illustrated in FIG. 4D as determined spectrographic content 430*c*. A center wavelength 431*c* of a peak of the determined spectrographic content 430*c* that corresponds to the second peak of the second spectrographic content 420*c* corresponds to the center wavelength 409*c* of the second peak shifted by an amount corresponding to the center wavelength 407*c* of the first peak of the first spectrographic content 410*c*.

Note that the detected and/or determined frequency and/or spectrographic content illustrated in FIGS. 4A-4D are non-limiting examples intended to illustrate a variety of methods that could be used to determine flow properties in biological tissue based on detected properties of two or more received lights emitted from the biological tissue in response to illumination of the biological tissue by respective two or more beams of coherent illumination that differ with respect to one or more properties (e.g., wavelength, coherence length, beam divergence). Such methods could be applied to a variety of different single-valued (e.g., intensities) and/or multiply-valued (e.g., spectrographic content characterized by the intensity of received light in a plurality of ranges of wavelengths) detected properties of received light. Further, such techniques could be applied to determined flow properties or other determined values (e.g., such techniques could be applied to flow rate spectra, blood cell velocity distributions, or other flow properties determined based on respective different received lights). Additional methods for determining flow properties in a biological environment based on such received lights are anticipated.

A target portion of the environment could comprise an overlap between first and second sets of elements of the environment respectively preferentially interacted with by the first and second beams of illumination. Alternatively, a target portion of the environment could comprise a set of elements of the environment preferentially interacted with by the first beam of illumination but not by the second beam of illumination. A target portion could comprise volume of the environment within a specified range of depths within the environment. A target portion could comprise a particular target tissue type, chemical, tissue or material layer, material, mineral, or some other element(s) of interest on or within the environment. For example, a target portion could include blood cells flowing in blood in portions of subsurface vasculature of a human body. In another example, a target portion could include blood cells flowing in blood and/or interstitial fluid in portions of a human body that are subject to a surgical intervention.

Determining a flow property in biological tissue (or some other environment of interest) could include determining one or more flow properties (e.g., a mean flow rate, a distribution of velocities of scatterers in a fluid flow) in a plurality of volumes, areas, or other regions of the biological tissue. For example, flow properties could be determined for a plurality of regions across an area of biological tissue, e.g., at a plurality of points having a regular spacing across the biological tissue. Such points could correspond to a plurality of portions of the biological tissue from which respective light-sensitive elements of an imager receive light (e.g., a target portion of tissue corresponding to an overlap between regions with which first and second beams of coherent illumination preferentially interact). Additionally or alternatively, flow properties could be determined for a plurality of regions within a volume of biological tissue, e.g., at a plurality of points having a regular or otherwise specified spacing within a specified distance from a surface of the biological tissue. Further, a resolution (i.e., a spacing between such points for which flow properties are determined) of such a determination could be related to the depth beneath a surface of the biological tissue. For example, a resolution at which flow properties can be determined in a biological tissue could reduce with increasing depth beneath a surface of the biological tissue due, e.g., to scattering of coherent illumination by elements in additional intervening portions of the biological tissue between a source of illumination and/or imager and such deeper tissues.

Determining flow properties for such a regular or otherwise spaced set of points in a biological tissue could allow for the determination of a map vasculature or other structures within the biological tissue. For example, the extent of different types of tissue and/or volumes within the biological tissue based on information about flow properties of such types of tissue or volumes. For example, the location, shape, or other properties of a tumor, neoplasm, cyst, anastomosis, aneurism, epileptic focus, or some other target of a surgical intervention could be determined based in part on a map of flow properties (e.g., flow rates of blood or other fluid) within and/or across the biological tissue. Such a determined map of flow properties could be used to generate a map of blood vessels within the tissue or some other information about the tissue and/or vasculature therein. For example, the depth of blood vessels, depth of regions of greater flow, flow rate pulsatility, blood cell oxygenation, or some other information could be mapped across and/or within the biological tissue. Further, such maps or other information about flow properties within and/or across the biological tissue could be used to determine the location, pattern, extent, depth beneath a surface of the biological tissue, or other properties of tissues, structures, or other elements within the biological tissue. Such maps could be two-dimensional (e.g., indicating the locations or other information about vasculature within a biological tissue relative to a two-dimensional surface, e.g., a surface of the biological tissue) or three-dimensional (reporting the trajectories and other information about the location and extent to vasculature throughout a volume of biological tissue).

Such determined maps or other information describing the location of vasculature in a biological tissue could be used in a variety of applications. A determined map of vasculature could be used to avoid damaging vasculature of a tissue when performing a surgical intervention in the tissue. For example, a surgeon and/or robotic surgical system could avoid ablating vasculature of a biological tissue when operating to ablate a target tissue (e.g., a tumor). Additionally or alternatively, a surgical plan could be determined based on a map of the vasculature to avoid disrupting or reducing perfusion to a particular region of tissue, e.g., a nerve, a portion of eloquent cortex, a functional portion of cardiac muscle.

Flow properties in a biological environment could be determined in a variety of ways from one or more detected properties (e.g., an intensity waveform, a frequency spectrum and/or content thereof of a time-varying pattern of constructive and destructive interference, a wavelength, a spectral content) of received first and second lights emitted from the biological environment in response to illumination by respective first and second beams of coherent illumination. In some examples, flow properties could be determined based on one or more detected properties of a received first light emitted from the environment in response to illumination by a first beam of coherent illumination. In some examples, flow properties could be determined based on one or more detected properties of a received first second lights emitted from the environment in response to illumination by first and second beams of coherent illumination, respectively (e.g., by determining an unwanted signal that is in-common between the first and second emitted lights and determining the flow property based on the signal detected from the first emitted light less the in-common signal).

In some examples, flow properties in first and second portions of the biological environment could be determined based on one or more detected properties of respective received first and second lights emitted from the environment in response to illumination by respective first and second beams of coherent illumination. A flow property of a target region (e.g., a region of overlap between the first and second portions of the biological environment) could then be determined based on the determined flow properties in the first and second portions of the biological environment. For example, a flow property of the target region could be determined by determining a property of flow that is in-common between the determined flow properties of the first and second portions of the biological environment (e.g., a velocity of the biological environment relative to a light source and light sensor configured to emit the first and second beams of illumination and to detect the first and second responsively emitted lights) and determining the flow property of the target region by removing (e.g., by subtraction) the in-common flow property from one of the determined flow properties of the first and second portions of the biological environment.

Flow properties in a portion of biological tissue (e.g., a portion with which a first beam of coherent illumination preferentially interacts) could be determined in a variety of ways based on a variety of detected properties of received light emitted in response to coherent illumination of the portion of biological tissue. For example, a time-varying or static pattern of constructive and destructive interference, an intensity, a wavelength, a linewidth, an optical spectrum, or other information or properties of the emitted light could be detected and used to determine flow properties in the biological tissue. Such properties could be detected at a single point in time, at a plurality of points in time, and/or a property of the change of such detected properties over time could be detected or determined and used to determine flow properties in the biological tissue. Additionally or alternatively, one or more such properties could be detected in a plurality of portion of light emitted from the biological tissue in response to coherent illumination, e.g., detected from a plurality of directions and/or from a plurality of emitting regions of the biological tissue (i.e., a light sensor could image the biological tissue).

For example, flow propertied in a portion of biological tissue could be determined by determining a contrast between one or more properties of light received from a number of different proximate portions of the biological tissue. This could include generating an image of the biological tissue by detecting an average intensity of the time-varying patterns of light received from a plurality of portions of the biological tissue over a specified period of time (e.g., an exposure duration). Contrast in such an image could be determined by a variety of methods (e.g., Weber contrast, Michelson contrast, RMS contrast) and used to determine a relative amount of flow in a portion of the biological tissue based on a determined amount of contrast in the image that corresponds to the portion of the biological tissue. One or more properties of the specified period of time (e.g., the exposure duration of the period of time) could be specified relative to an application (e.g., to set a level of flow detected using this method, a resolution of flow levels detected using this method). For example, an exposure duration could be approximately 50 milliseconds long to allow detection of flow properties based on the contrast of an image generated using such an exposure duration. Additionally or alternatively, a detected intensity, speckle rate, polarization, wavelength, spectrum, or other detected property of light received from a portion of biological tissue could be compared to detected properties of light received from surrounding portions to form a baseline or to allow some other determination, e.g., to determine a noise floor, to set a threshold, to normalize or otherwise scale detected properties, or according to some other application.

Further, such contrast or other spatial computations could be determined at a variety of spatial and temporal resolutions. For example, one or more properties (e.g., an average intensity of received light during a specified time period, a speckle event rate, a wavelength, a difference in wavelength relative to the wavelength of a corresponding beam of coherent illumination) of light received from each of a plurality of portions of the biological tissue could be averaged, smoothed, or otherwise resampled at a variety of different spatial resolutions, and statistical distributions of the one or more properties across the portions of the biological tissue at the variety of different resolutions could be determined and used to determine flow properties in the biological tissue. Further, such contrast or other spatial determinations could be determined based on detected properties of received light detected at a plurality of different exposures (or based on detected properties of received light applied to different filters, different filter settings, or across a change in some other analog or digital method of processing the detected properties) and flow properties in the biological environment could be determined based on such different determined contrast or other spatial determinations.

Frequency content (e.g., a frequency spectrum, a power within one or more ranges of frequencies) of one or more of the above described properties of received light (e.g., time-varying patterns of constructive and destructive interference, intensities, wavelengths, spectra) could be detected and/or determined and used to determine flow properties in a portion of biological tissue. Such determined properties could be used to determine a mean flow rate, a distribution of flow rates, a distribution of scatterer (e.g., blood cell) velocities within a flow, flow properties of multiple fluid flows within a single portion of tissue, or some other information about flow properties in the particular portion of biological tissue.

A flow property in a biological tissue at and/or within one or more depths and/or ranges of depths within the biological tissue or in some other specified region(s) in the biological tissue could be determined using the methods described above, some other methods, or a combination thereof. In some examples, a flow property (e.g., a flow rate of blood) within a specified range of depths within a biological tissue could be determined by illuminating the biological tissue with first and second beams of light having respective specified first and wavelengths, coherence lengths, or some other specified differing properties such that the flow property in tissue at the specified depth could be determined based on received first and second lights emitted responsively to the first and second beams of illumination. For example, the first and second wavelengths and/or coherence length could be specified such that the first beam of illumination preferentially interacts with tissue within a range of depths between a surface of the biological tissue and the shallow edge of the specified range of depths and such that the second beam of illumination preferentially interacts with tissue within a range of depths between the surface of the biological tissue and the deep edge of the specified range of depths. Thus, a difference in one or more detected properties of the responsively emitted respective first and second lights could correspond to flow properties at the specified depth within a biological tissue. This could include the first wavelength being shorter than the second wavelength, based on the reduced penetration depth of shorter wavelength light in turbid or otherwise scattering media like biological tissues.

Further, flow properties in biological tissue could be detected based on different detected properties of first and second (or more) lights emitted from the biological tissue in response to illumination by respective first and second (or more) beams of coherent illumination that differ in respect to one or more properties. Additional methods for determining flow properties in biological tissue based on such detected properties of responsively light emitted from the biological tissue in response to illumination by beams of coherent illumination are anticipated.

IV. Example Devices

Figure 5:
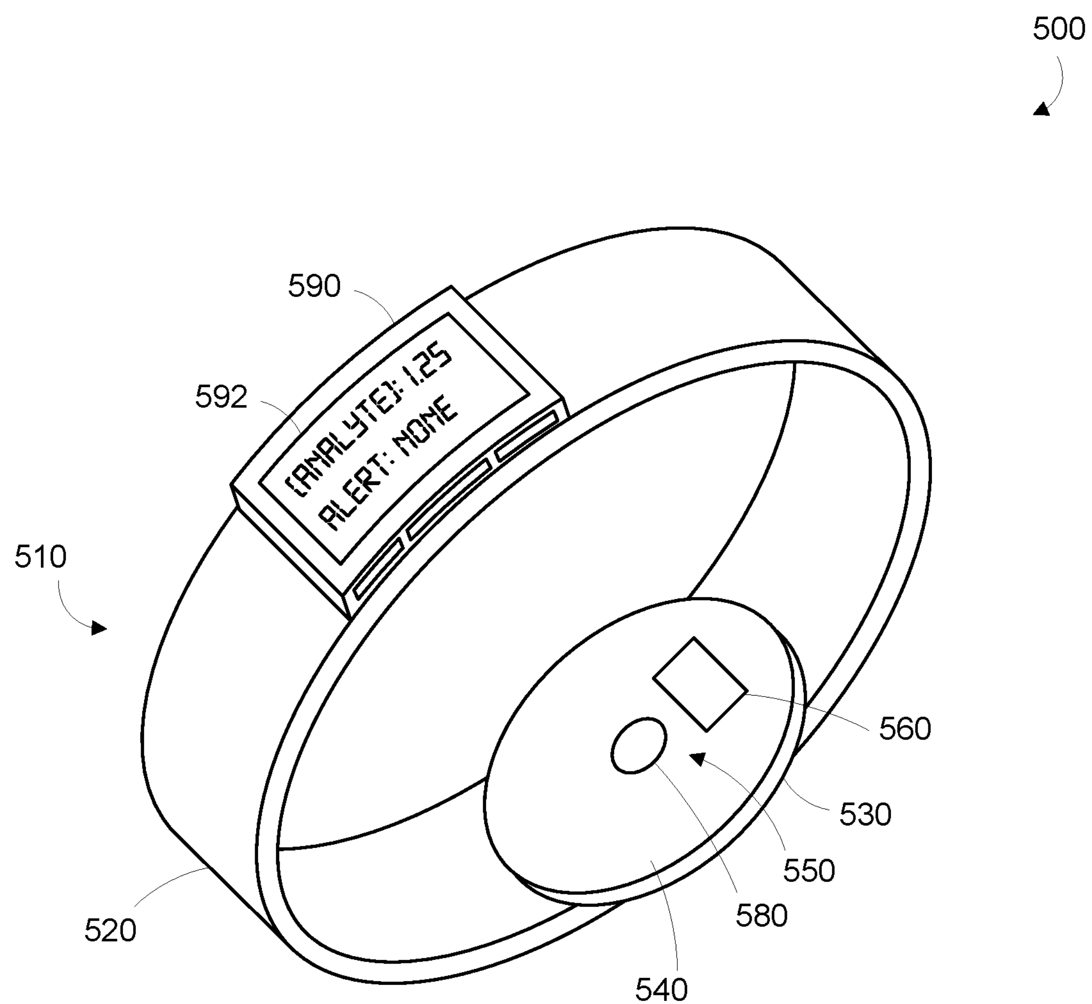
FIG. 5 is a perspective view of an example wearable device.

A wearable device 500 (illustrated in FIG. 5) can automatically measure a flow property of blood in a portion of subsurface vasculature (or of some other tissue or cells) of a person wearing the device. The term "wearable device," as used in this disclosure, refers to any device that is capable of being worn at, on or in proximity to a body surface, such as a wrist, ankle, waist, chest, or other body part. In order to take in vivo measurements in a non-invasive manner from outside of the body, the wearable device may be positioned on a portion of the body where subsurface vasculature is easily observable, the qualification of which will depend on the type of detection system used. The device may be placed in close proximity to the skin or tissue, but need not be touching or in intimate contact therewith. A mount 510, such as a belt, wristband, ankle band, etc. can be provided to mount the device at, on or in proximity to the body surface. The mount 510 may prevent the wearable device from moving relative to the body to reduce measurement error and noise. In one example, shown in FIG. 5, the mount 510, may take the form of a strap or band 520 that can be worn around a part of the body. Further, the mount 510 may be an adhesive substrate for adhering the wearable device 500 to the body of a wearer.

A measurement platform 530 is disposed on the mount 510 such that it can be positioned on the body where subsurface vasculature is easily observable. An inner face 540 of the measurement platform is intended to be mounted facing to the body surface. The measurement platform 530 may house a data collection system 550, which may include at least a light source 580 configured to emit first and second (or more) beams of coherent illumination that differ with respect to one or more properties (e.g., wavelength, linewidth, coherence length, spectral profile, angle relative to the portion of subsurface vasculature, beam divergence, beam shape) into a portion of subsurface vasculature. The measurement platform 530 additionally includes a light sensor 560 configured to detect one or more properties (e.g., a time-varying pattern of constructive and destructive interference, a wavelength, a difference in wavelength relative to a wavelength of a corresponding beam of illumination emitted by the lights source 580) of first and second (or more) light emitted from the portion of subsurface vasculature in response to respective first and second (or more) beams of coherent illumination emitted from the light source 580. In a non-exhaustive list, the light sensor 560 may include one or more of a photodiode, a phototransistor, a photoresistor, an active pixel sensor, a CCD, a camera, a spectrometer, an interferometer, or some other light sensitive element configured to detect one or more properties of the emitted light. The components of the data collection system 550 may be miniaturized so that the wearable device may be worn on the body without significantly interfering with the wearer's usual activities.

The data collection system 550 may additionally include additional detectors for detecting other physiological parameters, which could include any parameters that may relate to the health of the person wearing the wearable device. For example, the data collection system 550 could include detectors configured to measure blood pressure, pulse rate, respiration rate, skin temperature, etc. In a non-exhaustive list, additional detectors may include any one of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor.

The light source 580 is configured to transmit beams of coherent illumination that can penetrate the wearer's skin into the portion of subsurface vasculature, for example, into a lumen of the subsurface vasculature. The transmitted illumination can be any kind of illumination that is benign to the wearer and that results at least in scattering of the beam of illumination to produce light responsively emitted from the body having one or more detectable properties related to flow properties in the portion of subsurface vasculature (e.g., a time-varying pattern of constructive and destructive interference, a wavelength, a spectrum). The wavelength of the transmitted illumination could be specified to penetrate biological tissues of a wearer; for example, the transmitted illumination could have a wavelength within a near-infrared (NIR) transparency window of biological tissue (e.g., between approximately 650 nanometers and approximately 950 nanometers and/or between approximately 1000 nanometers and approximately 1350 nanometers). The wavelength of the transmitted illumination could be specified to be a wavelength that is scattered by blood cells. The wavelength of the transmitted illumination could be between approximately 400 nanometers and approximately 1000 nanometers.

The wearable device 500 may also include a user interface 590 via which the wearer of the device may receive one or more recommendations or alerts generated either from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 590 may include a display 592 where a visual indication of the alert or recommendation may be displayed. The display 592 may further be configured to provide an indication of the measured physiological parameters, for instance, a determined rate of flow of blood in a portion of subsurface vasculature.

Figure 6A:
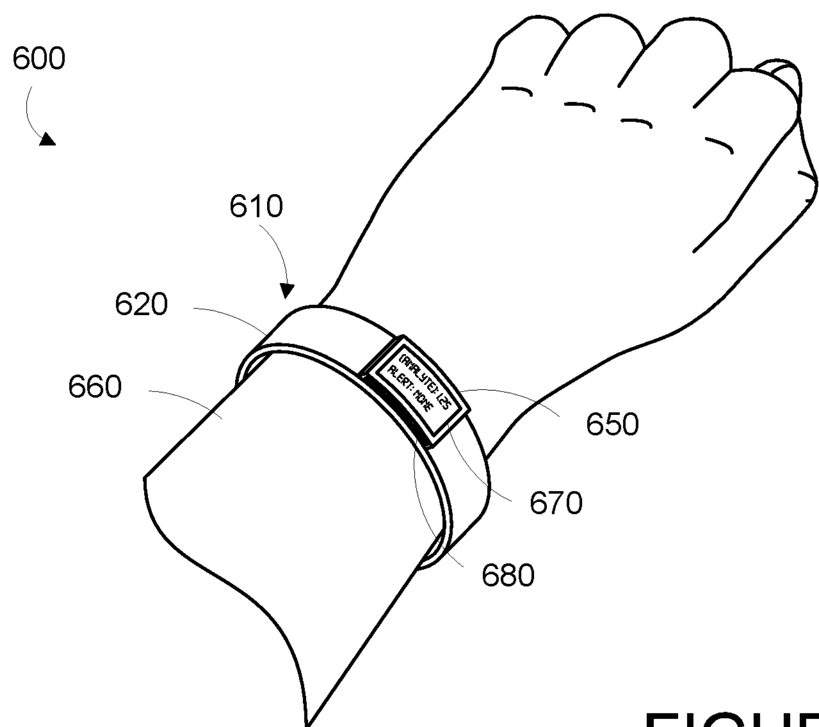
FIG. 6A is a perspective top view of an example wrist-mounted device, when mounted on a wearer's wrist.
Figure 6B:
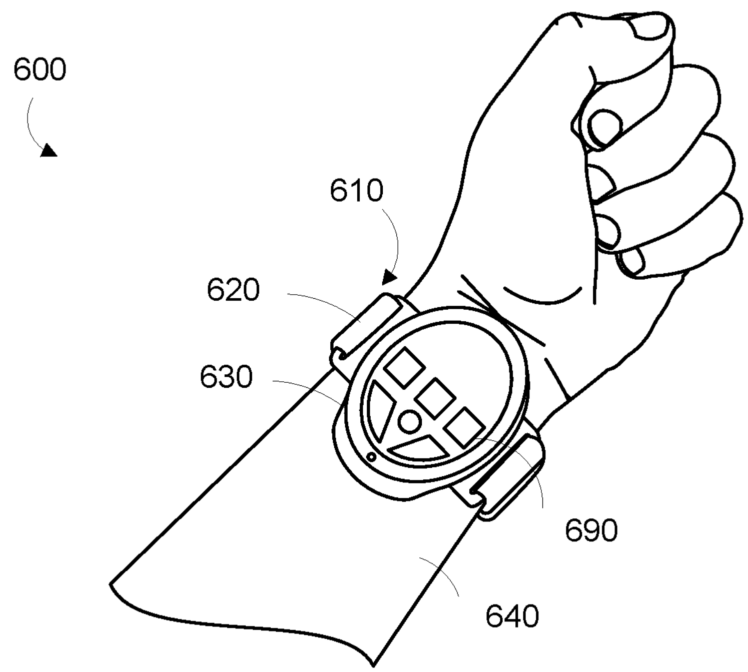
FIG. 6B is a perspective bottom view of an example wrist-mounted device shown in FIG. 6A, when mounted on a wearer's wrist.

In some examples, the wearable device is provided as a wrist-mounted device, as shown in FIGS. 6A and 6B. The wrist-mounted device may be mounted to the wrist of a living subject with a wristband or cuff, similar to a watch or bracelet. As shown in FIGS. 6A and 6B, the wrist mounted device 600 may include a mount 610 in the form of a wristband 620, a measurement platform 630 positioned on the anterior side 640 of the wearer's wrist, and a user interface 650 positioned on the posterior side 660 of the wearer's wrist. The wearer of the device may receive, via the user interface 650, one or more recommendations or alerts generated either from a remote server or other remote computing device, or alerts from the measurement platform. Such a configuration may be perceived as natural for the wearer of the device in that it is common for the posterior side 660 of the wrist to be observed, such as the act of checking a wrist-watch. Accordingly, the wearer may easily view a display 670 on the user interface. Further, the measurement platform 630 may be located on the anterior side 640 of the wearer's wrist where the subsurface vasculature may be readily observable. However, other configurations are contemplated.

The display 670 may be configured to display a visual indication of the alert or recommendation and/or an indication of the measured physiological parameters, for instance, the flow rate or other flow property of blood in a portion of subsurface vasculature of the wearer. Further, the user interface 650 may include one or more buttons 680 for accepting inputs from the wearer. For example, the buttons 680 may be configured to change the text or other information visible on the display 670. As shown in FIG. 6B, measurement platform 630 may also include one or more buttons 690 for accepting inputs from the wearer. The buttons 690 may be configured to accept inputs for controlling aspects of the data collection system, such as initiating a measurement period, or inputs indicating the wearer's current health state (i.e., normal, migraine, shortness of breath, heart attack, fever, "flu-like" symptoms, food poisoning, etc.).

Figure 7:
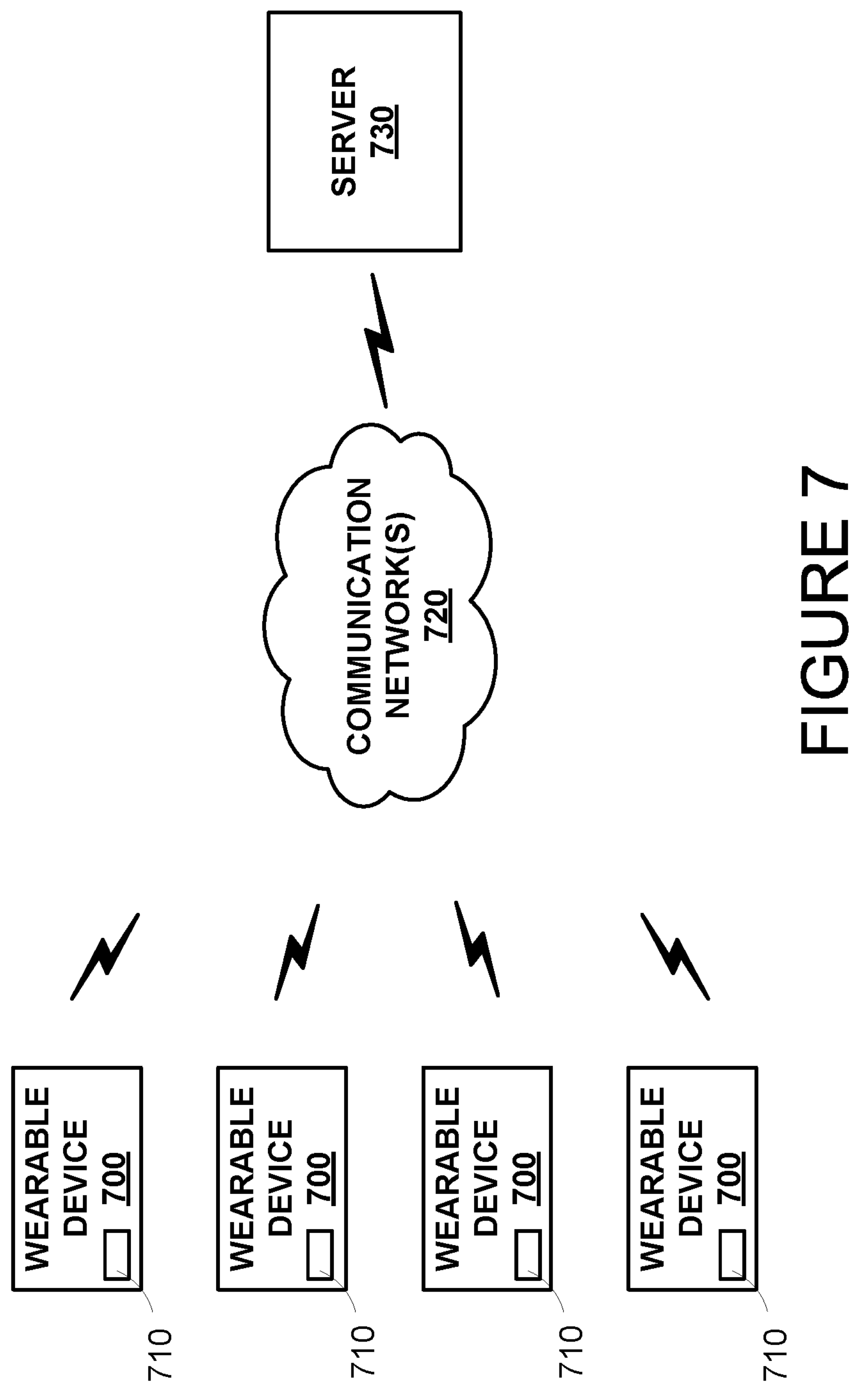
FIG. 7 is a block diagram of an example system that includes a plurality of wearable devices in communication with a server.

FIG. 7 is a simplified schematic of a system including one or more wearable devices 700. The one or more wearable devices 700 may be configured to transmit data via a communication interface 710 over one or more communication networks 720 to a remote server 730. In one embodiment, the communication interface 710 includes a wireless transceiver for sending and receiving communications to and from the server 730. In further embodiments, the communication interface 710 may include any means for the transfer of data, including both wired and wireless communications. For example, the communication interface may include a universal serial bus (USB) interface or a secure digital (SD) card interface. Communication networks 720 may be any one of may be one of: a plain old telephone service (POTS) network, a cellular network, a fiber network and a data network. The server 730 may include any type of remote computing device or remote cloud computing network. Further, communication network 720 may include one or more intermediaries, including, for example wherein the wearable device 700 transmits data to a mobile phone or other personal computing device, which in turn transmits the data to the server 730.

In addition to receiving communications from the wearable device 700, such as collected physiological parameter data and data regarding health state as input by the user, the server may also be configured to gather and/or receive either from the wearable device 700 or from some other source, information regarding a wearer's overall medical history, environmental factors and geographical data. For example, a user account may be established on the server for every wearer that contains the wearer's medical history. Moreover, in some examples, the server 730 may be configured to regularly receive information from sources of environmental data, such as viral illness or food poisoning outbreak data from the Centers for Disease Control (CDC) and weather, pollution and allergen data from the National Weather Service. Further, the server may be configured to receive data regarding a wearer's health state from a hospital or physician. Such information may be used in the server's decision-making process, such as recognizing correlations and in generating clinical protocols.

Additionally, the server may be configured to gather and/or receive the date, time of day and geographical location of each wearer of the device during each measurement period. Such information may be used to detect and monitor spatial and temporal spreading of diseases. As such, the wearable device may be configured to determine and/or provide an indication of its own location. For example, a wearable device may include a GPS system so that it can include GPS location information (e.g., GPS coordinates) in a communication to the server. As another example, a wearable device may use a technique that involves triangulation (e.g., between base stations in a cellular network) to determine its location. Other location-determination techniques are also possible.

The server may also be configured to make determinations regarding the efficacy of a drug or other treatment based on information regarding the drugs or other treatments received by a wearer of the device and, at least in part, the physiological parameter data and the indicated health state of the user. From this information, the server may be configured to derive an indication of the effectiveness of the drug or treatment. For example, if a drug is intended to treat nausea and the wearer of the device does not indicate that he or she is experiencing nausea after beginning a course of treatment with the drug, the server may be configured to derive an indication that the drug is effective for that wearer. In another example, a wearable device may be configured to measure blood glucose. If a wearer is prescribed a drug intended to treat tachycardia, but the server receives data from the wearable device indicating (based on a plurality of determined flow properties determined at respective points in time in portions of subsurface vasculature of the wearer) that the wearer's heart rate has remained elevated over a certain number of measurement periods, the server may be configured to derive an indication that the drug is not effective for its intended purpose for this wearer.

Further, some embodiments of the system may include privacy controls which may be automatically implemented or controlled by the wearer of the device. For example, where a wearer's collected physiological parameter data and health state data are uploaded to a cloud computing network for trend analysis by a clinician, the data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined.

Additionally or alternatively, wearers of a device may be provided with an opportunity to control whether or how the device collects information about the wearer (e.g., information about a user's medical history, social actions or activities, profession, a user's preferences, or a user's current location), or to control how such information may be used. Thus, the wearer may have control over how information is collected about him or her and used by a clinician or physician or other user of the data. For example, a wearer may elect that data, such as health state and physiological parameters, collected from his or her device may only be used for generating an individual baseline and recommendations in response to collection and comparison of his or her own data and may not be used in generating a population baseline or for use in population correlation studies.

Figure 8:
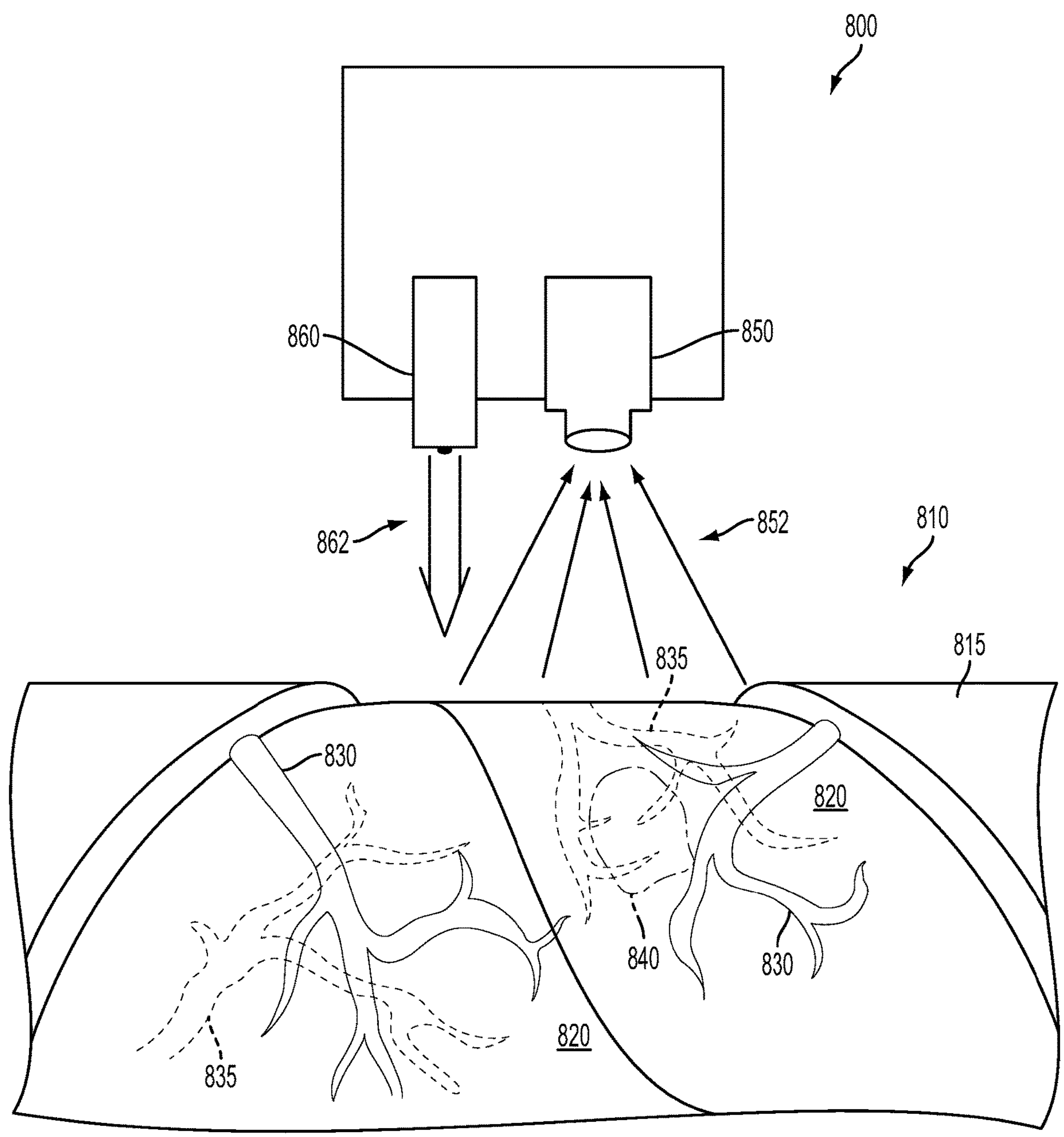
FIG. 8 is a perspective view of an example device, while measuring fluid flow in biological tissue.

A device 800 as illustrated in FIG. 8 can determine flow properties (e.g., a flow rate, a velocity of one or more particles in a fluid flow, or some other properties of flow at and/or through one or more locations or regions) in a biological tissue 810 by emitting first and second (or more) beams of coherent illumination 862 that differ with respect to one or more properties (e.g., wavelength, linewidth, coherence length, spectral profile, angle relative to the portion of subsurface vasculature, beam divergence, beam shape) into the biological tissue 810 using a light source 860 and detecting one or more properties (e.g., time-varying patterns of constructive and destructive interference, wavelengths, spectra) of first and second (or more) emitted lights 852 that are emitted from a plurality of portions (e.g., areas) of the biological tissue 510 in response to illumination by respective first and second (or more) beams of coherent illumination 862 using an imager 850. The biological tissue 810 can be any environment containing scatterers (e.g., blood cells, other cells, organelles, cell walls, vessel walls) such that the scatterers and other elements of the biological tissue 810 scatter the beams of coherent light 862 in a manner that causes the emitted lights 852 to have one or more properties related to flow properties in the biological tissue 810.

As illustrated in FIG. 8, the biological tissue 810 includes biological tissues undergoing a surgical intervention. The biological tissue 810 includes skin 815 that has been cut and retracted to expose underlying tissues that could be subject to further surgical intervention. The underlying tissues include bulk tissue 820 (e.g., muscle tissue, brain tissue, liver tissue, breast tissue, or some other biological tissue(s)) and a target tissue 840 (e.g., a tumor, neoplasm, cyst, anastomosis, aneurism, epileptic focus, or some other target of a surgical intervention) within the bulk tissue 820. Surface vessels 830 and deep vessels 835 are present on the surface of and within the bulk tissue, respectively. Flow properties in the biological tissue 810 could be detected for surface regions of the biological tissue 810 (e.g., for fluid flows within the surface vessels 830 and/or in interstitial tissue, capillary beds, and/or microvasculature near the surface of the bulk tissue 820) and/or for deeper tissues. Further, the device 800 could be configured to detect flow properties of biological tissues through overlying tissues. In some examples, flow properties in the bulk tissue 820, vessels 835, 835, and/or target tissue 840 could be detected and/or determined by illuminating and detecting light emitted from such tissues through a layer of overlying tissue such that such flow properties could be detected and/or determined without cutting through and/or retracting the skin 815.

The imager 850 and light source 860 could be configured as illustrated in FIG. 8 (i.e., separate, parallel, non-coaxial) or could be configured in another way, according to an application. In some examples, the imager 850 and light source 860 could be coupled to a set of optical elements to enable some function. In an example, the direction of the beams of coherent illumination 862 emitted by the light source 860 could be controllable using some apparatus, for example a set of galvanometer-driven mirrors. The galvanometers could be operated such that flow properties in specified regions (where the beam from the light source is directed) could be illuminated such that flow properties in the specified regions could be determined. Other configurations and applications are anticipated. In some examples, a flow property in a particular portion of (e.g., within a specified range of depths within) and/or of a particular set of elements of (e.g., blood in the surface 830 and/or deep 835 vessels) the biological environment 810 could be detected by specifying one or more properties of the first and second beams of coherent illumination relative to properties of the particular portion of and/or set of elements of the biological tissue 810.

For example, a first wavelength of the first beam of illumination and a second wavelength of the second beam of illumination could be specified such that the first wavelength is shorter than the second wavelength. The first wavelength could be specified such that the first beam preferentially interacts with elements of the biological tissue 810 within a first range of depths from the surface of the biological tissue 810 that does not include depths within which the deep vessels 835 are located and the second wavelength could be specified such that the second beam preferentially interacts with elements of the biological tissue 810 within a second range of depths that includes depths within which the deep vessels 835 are located in addition to the first range of depths. In such an example, light emitted from the biological tissue 810 in response to illumination by the first and second beams of illumination could be detected and used to determine flow properties within the range of depths within which the deep vessels 835 are located (e.g., to determine flow properties of blood within the deep vessels 835). Additionally or alternatively, in such an example the first and second beams of coherent illumination could have respective different coherence lengths, where the coherence length of the first beam is shorter than the coherence length of the second beam. Other examples of differences in properties of first and second (or more) beams of illumination specified to determined flow properties of/in different sets of elements and/or portions of a biological environment are anticipated.

The imager 850 is configured to detect one or more properties (e.g., time-varying patterns of constructive and destructive interference, wavelengths, spectra) of lights emitted from a plurality of portions of the biological tissue 810 in response to illumination by respective beams of coherent illumination emitted from the light source 880. In a non-exhaustive list, the imager 850 may include one or more photodiodes, phototransistors, photoresistors, active pixel sensors, CCDs, cameras, angle-sensitive pixels, spectrometers, interferometers, or some other light-sensitive elements configured to detect one or more properties of light emitted from respective portions of the biological tissue 810. The components of the device 800 may be miniaturized so that the device 800 may be used to detect flow properties in the biological tissue 810 while minimally impeding access to the biological tissue 810, e.g., to cut, ablate, resect, retract, palpate, cauterize, suture, clamp, or otherwise manipulate or interact with the biological tissue 810.

The light source 860 and/or imager 850 could include one or more lenses, filters, collimators, diffraction gratings, or other elements according to an application. For example, the imager 860 could include a filter such that light-sensitive elements of the imager 850 only receive light at wavelengths corresponding to wavelengths of beams of coherent light 862 emitted by the light source 860. In another example, the light source 860 could include a polarizing filter or could be otherwise configured such that the emitted beams of coherent illumination 862 are polarized in a first specified direction. The imager 850 could also include a polarizing filter or other optical element(s) such that light-sensitive elements of the imager 850 are prevented from receiving light emitted from the biological tissue 810 that is polarized in the first specified direction (e.g., the imager 850 could include a polarizing filter that is oriented perpendicularly to the first specified direction). When the device 800 is configured in such a manner, light-sensitive elements of the imager 850 could be substantially prevented from receiving light from the light source 860 that is directly reflected from the surface of the biological tissue 810 (e.g., light from specular reflections). This could increase a signal-to-noise ratio of signals generated by light-sensitive elements of the imager 850 by increasing the contribution of scattered light to the signals relative to the contribution of specular reflection light that is not related to flow properties in the biological tissue 810.

The device 800 could be configured to emit the first and second (or more) beams of coherent illumination 862 at two or more respective different specified properties (e.g., wavelengths, coherence lengths, beam divergences) during two or more different periods of time. This could include the light source 860 being a tunable laser such that one or more properties (e.g., a cavity length, a gain medium refractive index, a reflectivity spectrum of a mirror) of the light source 860 are controllable to control the wavelength of coherent illumination emitted by the light source. In another example, the light source 860 could be configured to emit beams of coherent illumination having a controllable coherence length from a single laser. This could include the laser being configured to detune a cavity of the laser to decrease the coherence length of the illumination emitted by the laser by, e.g., controlling a cavity length or a gain medium refractive index. The laser could be a tunable laser (i.e., able to be operated to control a wavelength of the illumination output by the laser) and the coherence length of the illumination emitted by the laser could be decreased by changing the controlled wavelength of the laser around a specified wavelength at a high frequency. The coherence length of the laser could be controlled by injecting a carrier beam of illumination into the laser, by modulating the output of the carrier at a high frequency, or by some other method. Additionally or alternatively, first and second (or more) emitted beams of coherent illumination 862 differing with respect to one or more properties could include the light source 860 including two more different lasers or other coherent-light-emitting elements configured to emit respective first and second (or more) beams of coherent illumination that differ with respect to the one or more properties.

Further, emitting beams of coherent illumination 862 at two or more different wavelengths during two or more different periods of time could allow for determination of spectrographic properties of the biological tissue 810. For example, a reflectivity, absorption, scattering, excitation, emission, or other type of spectrum or spectrographic information could be determined for regions of the biological tissue 810. Such determined spectrographic information could be used to determine flow properties in the biological tissue 810 or to determine some other information about the biological tissue 810. For example, the device 800 could emit first and second beams of coherent illumination (e.g., from respective first and second lasers of the device 800) at respective different first and second wavelengths (e.g., at a red wavelength and a near-infrared wavelength). A level of blood cell oxygenation in one or more particular regions of the biological tissue 810 (e.g., within surface 830 and/or deep 835 vessels) could be determined based on properties (e.g., intensities) of light emitted from the one or more particular regions of the biological tissue 810 in response to illumination by the first and second beams of illumination (e.g., based on knowledge of absorption spectra of oxygenated and of deoxygenated hemoglobin in blood cells). Other applications of spectrographic information about the biological tissue 810 detected using the device 800 are anticipated.

The light source 860 is configured to transmit a beam of coherent illumination 862 that can penetrate the biological tissue 810, for example, into a lumen of vessels on the surface and/or within the bulk tissue 810. The transmitted illumination can be any kind of illumination that is benign to the biological tissues 820 and that results at least in scattering of the beam of illumination to produce time-varying patterns of constructive and destructive interference in light emitted from the biological tissue that are related to the disposition of scatterers (e.g., blood cells) in fluid flows (e.g., blood flows, interstitial fluid flows) in the biological tissue 810. The wavelength of the transmitted illumination could be specified to penetrate biological tissues; for example, the transmitted illumination could have a wavelength within a near-infrared (NIR) transparency window of biological tissue (e.g., between approximately 650 nanometers and approximately 950 nanometers and/or between approximately 1000 nanometers and approximately 1350 nanometers). The wavelength of the transmitted illumination could be specified to be a wavelength that is scattered by blood cells. The wavelength of the transmitted illumination could be between approximately 400 nanometers and approximately 1000 nanometers.

The device 800 could be secured relative to the biological tissue 810 and/or some other tissues and/or surgical instrument(s) in a variety of ways. The components of the device 800 may be disposed on or within a mount or housing or on some other structure for mounting the device 800 to enable stable detection of flow properties in the biological tissue 810 or other functions relative to elements in a surgical environment, for example, to a surgical frame secured relative to the biological tissue 810 located within a body cavity that is subject to a surgical intervention. The surgical system 800 could include additional components. Device 800 may take a variety of forms, such as a wall, surgical table, ceiling, or floor-mounted device. Device 800 could also take the form of a system, device, or combination of devices that is configured to be part of another device, apparatus, or system. For example, device 800 could take the form of an imager, laser, and/or other components configured to be mounted to or otherwise disposed as part of a surgical apparatus, tool, implement, or system (e.g., a robotic surgical system, a stereotactic surgical apparatus, a laparoscopic and/or endoscopic surgical system). Device 800 could also take the form of a system configured to detect flow properties in some other industrial environment, medical environment, scientific environment, or some other environment. Surgical Device 400 could also take other forms A device as described herein (e.g., 800) could be configured to determine and/or detect flow properties in a biological tissue (e.g., 810) as illustrated herein, or could be configured and/or operated to determine and/or detect flow properties in some other environment of interest. The device 800 could be configured to determine flow properties in a variety of portions/volumes across and/or throughout the biological tissue 810 in order to determine a map of flow throughout the biological tissue 810 (e.g., to determine a flow map of the tissue such that higher flow regions, e.g., vasculature on 830 or within 835 the bulk tissue 820, could be detected, identified, mapped, or otherwise determined). The environment could be an in vivo biological environment (e.g., a tissue of a living human, animal, plant, etc.) or an in vitro environment. The environment could be a biological sample in a sample container, cuvette, pipette, microscope slide, or other vessel. The environment could be part of a biological or chemical process. For example, the environment could be a fluid in a water treatment process, a fluid in a food or drug preparation process, a lake, stream, or river in a natural environment, or some other environment. The environment could be one or more portions of a microfluidic assay, process, or other microfluidic assembly. The environment could include a liquid, a gel, or some other phase of matter or combination of phases (e.g., an emulsion). The environment could include biological samples that had been freeze-dried, desiccated, frozen, vaporized, alkalated, or otherwise prepared, including adding natural and/or artificial scatterers to the environment.

V. Example Electronics Platform for a Device

Figure 9:
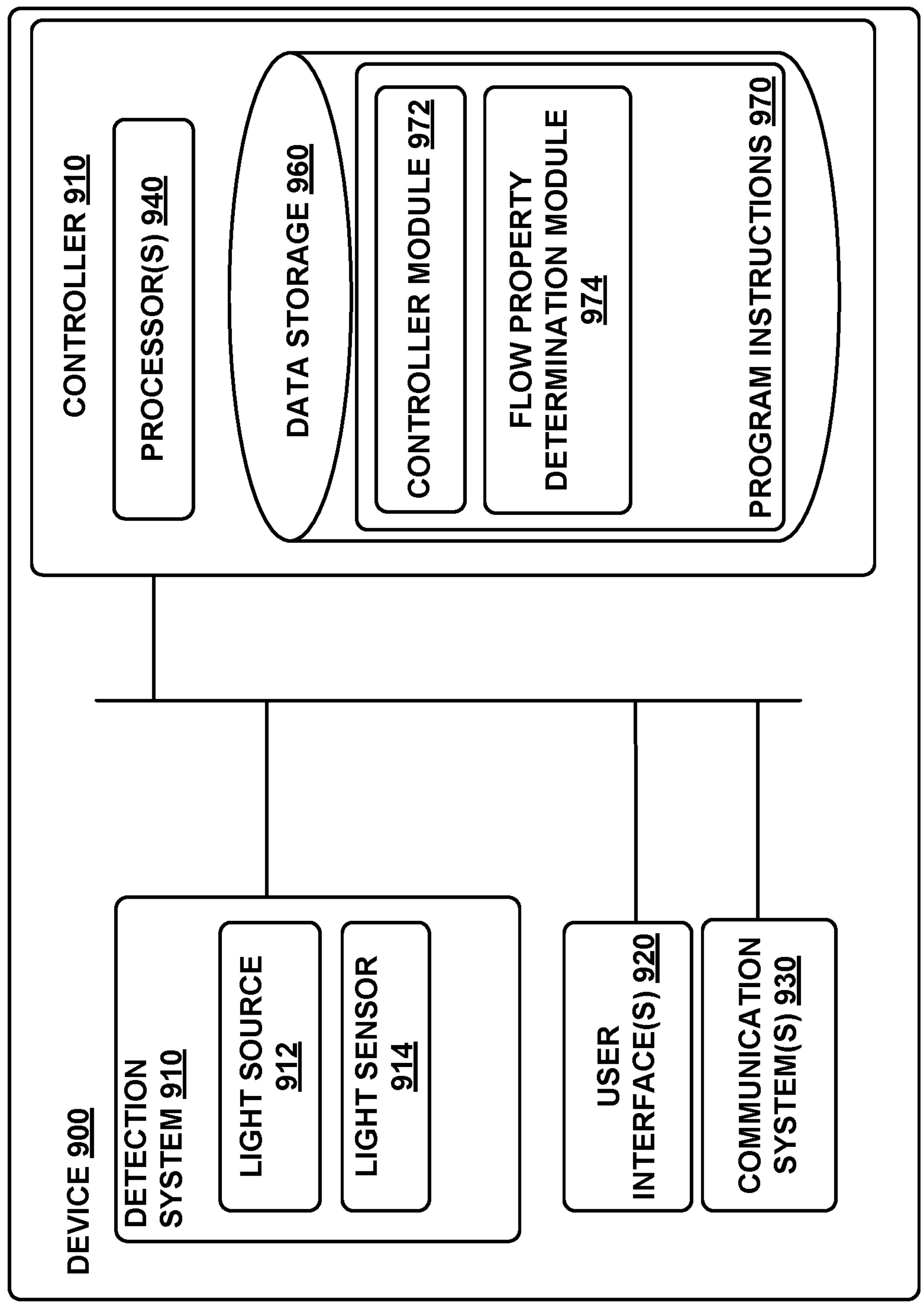
FIG. 9 is a functional block diagram of an example device.

FIG. 9 is a simplified block diagram illustrating the components of a device 900, according to an example embodiment. Device 900 may take the form of or be similar to the devices 100, 200*a*, 200*b*, 300, 500, 600, 800 shown in FIGS. 1, 2A, 2B, 3A-C, 5, 6A, 6B, and 8. In some examples, device 900 could take the form of a device configured to be secured relative to biological tissues undergoing a surgical intervention (e.g., tissue of a human body). For example, the device 900 could be configured to be mounted to a surgical frame, a floor, wall, ceiling, or other structure in a surgical environment or operating room, or secured to some other structure. In some examples, the device 900 could be configured to be secured to and/or a part of an endoscope, laparoscope, thoracoscope, or other surgical instrument configured to be inserted into a body cavity. In some examples, the device 900 could be part of a robotic surgical system and/or could be operated to inform the automated or semi-automated operation of such a system. Additionally or alternatively, the device 900 could be part of a robotic surgical system and information generated by the device could be indicated or otherwise presented to a surgeon or other operator of such a robotic surgical system (e.g., indicated on a display of a control console of such a robotic surgical system) to inform the performance of a surgical intervention by the surgeon. However, device 900 may also take other forms, e.g., could take the form of a device configured to be maintained in proximity to some other environment of interest (e.g., a body part, a biological sample container, a volume of a water treatment system) by a user or operator of the device 900 or by a frame or other supporting structure. Device 900 could also take the form of a device configured to illuminate and to detect emitted light from an in vitro biological environment or some other environment, for example, a fluid volume within a water treatment process, a microfluidic environment or assay, or some other environment. Device 900 also could take other forms.

In particular, FIG. 9 shows an example of a device 900 having a detection system 910, a user interface 920, communication system(s) 930 for transmitting data to a remote system, and controller 910. The components of the device 900 may be disposed on a mount or on some other structure for mounting the device to enable stable detection of flow properties in an environment of interest, for example, around a wrist of a wearer such that a portion of subsurface vasculature is visible.

Controller 910 may be provided as a computing device that includes one or more processors 940. The one or more processors 940 can be configured to execute computer-readable program instructions 970 that are stored in the computer readable data storage 960 and that are executable to provide the functionality of a device 900 described herein.

The computer readable data storage 960 may include or take the form of one or more non-transitory, computer-readable storage media that can be read or accessed by at least one processor 940. The one or more computer-readable storage media can include volatile and/or non-volatile storage components, such as optical, magnetic, organic or other memory or disc storage, which can be integrated in whole or in part with at least one of the one or more processors 940. In some embodiments, the computer readable data storage 960 can be implemented using a single physical device (e.g., one optical, magnetic, organic or other memory or disc storage unit), while in other embodiments, the computer readable data storage 960 can be implemented using two or more physical devices.

Detection system 910 includes a light sensor 914 and a light source 912. The light source 912 is configured to emit first and second (or more) beams of coherent illumination that differ with respect to one or more properties (e.g., wavelength, linewidth, coherence length, spectral profile, angle relative to the portion of subsurface vasculature, beam divergence, beam shape) into an environment of interest (e.g., into a biological tissue). The detection system 910 additionally includes a light sensor 914 configured to detect one or more properties (e.g., a time-varying pattern of constructive and destructive interference, a wavelength, a difference in wavelength relative to a wavelength of a corresponding beam of illumination emitted by the lights source 912) of first and second (or more) light emitted from the portion of subsurface vasculature in response to respective first and second (or more) beams of coherent illumination emitted from the light source 912. In a non-exhaustive list, the light sensor 914 may include one or more of a photodiode, a phototransistor, a photoresistor, an active pixel sensor, a CCD, a camera, a spectrometer, an interferometer, or some other light sensitive element configured to detect one or more properties of the emitted light.

The detection system 910 may additionally include additional detectors for detecting other properties of the environment of interest (e.g., for detecting physiological parameters of a human whose body includes the environment of interest). Such additional detected properties could include any parameters that may relate to the health of the person whose biological tissues are being measured by the device 900. For example, the detection system 910 could include detectors configured to measure blood pressure, pulse rate, respiration rate, skin temperature, etc. In a non-exhaustive list, additional detectors may include any one of an optical (e.g., CMOS, CCD, photodiode), acoustic (e.g., piezoelectric, piezoceramic), electrochemical (voltage, impedance), thermal, mechanical (e.g., pressure, strain), magnetic, or electromagnetic (e.g., magnetic resonance) sensor.

The detection system 910 could additionally include electronics configured to operate the light source 912 and the light sensor 914. The electronics could include a high-speed analog-to-digital converter (ADC) configured to sample an output (e.g., a voltage, a current) of one or more light-sensitive elements of the light sensor 914 at a specified high rate (e.g., one megahertz) to detect features of individual speckle events or other features in the output of the light-sensitive elements of the light sensor 914 that have one or more properties (e.g., a pulse width, a rise time, a rise rate, a time-varying pattern of constructive and destructive interference, a wavelength, a spectrum) related to flow properties in an environment of interest. Additionally or alternatively, the electronics could include analog frontend circuitry that includes analog circuitry configured to filter, decimate, quantize, or otherwise alter and/or perform other analog operations or computations on the output(s) of the light source 914 to produce an output electronic signal that is related to flow properties in the environment (e.g., flow properties in a portion of vasculature). This output electronic signal(s) could then be used (e.g., sampled by an ADC of a microcontroller) to determine the flow properties.

The program instructions 970 stored on the computer readable data storage 960 may include instructions to perform any of the methods described herein. For instance, in the illustrated embodiment, program instructions 970 include a controller module 972 and a flow property determination module 974.

The controller module 972 can include instructions for operating the detection system 910, for example, the light source 912 and the light source 914. For example, the controller module 972 may operate the light source 912 and the light sensor 914 during each of a set of pre-set measurement periods. In particular, the controller module 972 can include instructions for operating the light source 912 to emit first and second (or more) beams of coherent illumination that differ with respect to one or more properties (e.g., wavelength, coherence length, beam divergence) into a target environment (e.g., tissue of a person) and controlling the light sensor 914 to detect properties of first and second (or more) lights emitted from the environment responsive to respective first and second (or more) beams of illumination.

The controller module 972 can also include instructions for operating a user interface 920. For example, controller module 972 may include instructions for displaying data collected by the detection system 910 and analyzed by the flow property determination module 974. Further, controller module 972 may include instructions to execute certain functions based on inputs accepted by the user interface 920, such as inputs accepted by one or more buttons or touchscreen displays disposed on the user interface.

Flow property determination module 974 may include instructions for receiving data from and/or operating the data collection system 910, analyzing the data to determine flow properties in the environment (e.g., a flow rate of blood in a portion of vasculature, a flow rate of blood within a specified range of depths within the environment of interest), analyzing the determined flow properties to determine a map of vasculature and/or the location and extent of a target tissue, if a medical condition is indicated (e.g., a hemorrhage, a cessation of perfusion to a sensitive tissue), or other analytical processes relating to the environment proximate to the device 900. In particular, the flow property determination module 974 may include instructions for determining flow properties (e.g., flow rates, mean flow rates, velocities of one or more particles in one or more fluid flows, distributions of particle velocities in fluid flows) in the environment based on detected properties of first and second (or more) lights emitted from the environment responsive to respective first and second (or more) beams of coherent illumination.

Some of the program instructions of the controller module 972 and the flow property determination module 974 may, in some examples, be stored in a computer-readable medium and executed by a processor located external to the device 900. For example, the device 900 could be configured to illuminate and to receive light from portion of biological tissue and then transmit related data to a remote server, which may include a mobile device, a personal computer, the cloud, or any other remote system, for further processing (e.g., for the determination of frequency content of the received light, for determining flow properties in the biological environment, for determining the location and other information about blood vessels or other structures of the biological environment based on the determined flow properties).

User interface 920 could include indicators, displays, buttons, touchscreens, head-mounted displays, displays of a console of a tele-surgical system, and/or other elements configured to present information about the device 900 to a user and/or to allow the user to operate the device 900. Additionally or alternatively, the device 900 could be configured to communicate with another system (e.g., a cellphone, a tablet, a computer, a remote server) and to present elements of a user interface using the remote system. The user interface 920 could be disposed proximate to the light source 912, light sensor 914, or other elements of the device 900 or could be disposed away from other elements of the device 900 and could further be in wired or wireless communication with the other elements of the device 900. The user interface 920 could be configured to allow a user to specify some operation, function, or property of operation of the device 900. The user interface 920 could be configured to present information about a biological tissue or other contents of a surgical environment (e.g., a map of vasculature, a presence of a target tissue) to the user using a display, to present a determined flow property in a portion of subsurface vasculature or some other health state of a wearer of the device 900, or to present some other information to a user. Other configurations and methods of operation of a user interface 920 are anticipated.

Communication system(s) 930 may also be operated by instructions within the program instructions 970, such as instructions for sending and/or receiving information via a wireless antenna, which may be disposed on or in the device 900. The communication system(s) 930 can optionally include one or more oscillators, mixers, frequency injectors, etc. to modulate and/or demodulate information on a carrier frequency to be transmitted and/or received by the antenna. In some examples, the device 900 is configured to indicate an output from the controller 910 by transmitting an electromagnetic or other wireless signal according to one or more wireless communications standards (e.g., Bluetooth, WiFi, IRdA, ZigBee, WiMAX, LTE). In some examples, the communication system(s) 930 could include one or more wired communications interfaces and the device 900 could be configured to indicate an output from the controller 910 by operating the one or more wired communications interfaces according to one or more wired communications standards (e.g., USB, FireWire, Ethernet, RS-232).

The computer readable data storage 960 may further contain other data or information, such as scattering, absorption, or other optical properties of tissues of a user of the device 900, that may be useful in determining flow properties. Further, the computer readable data storage 960 may contain data corresponding to certain tissue optical or other property baselines that describe expected optical or other properties of biological tissues. The baselines may be pre-stored on the computer readable data storage 960, may be transmitted from a remote source, such as a remote server, or may be generated by the flow property determination module 974 itself. The flow property determination module 974 may include instructions for generating individual baselines for the user of the device 900 based on data collected over a certain number of measurement periods. For example, the flow property determination module 974 may generate a baseline tissue scattering and/or absorption spectrum based on detected time-varying patterns of constructive and destructive interference in light received from portions of a biological tissue (e.g., from portions proximate to a portion of vasculature that has been determined and/or that has been indicated, e.g., by a surgeon, to be on the surface of the biological tissue), and store those baselines in the computer readable data storage 960 for later use (e.g., to determine a depth of a portion of vasculature within the biological tissue). Baselines may also be generated by a remote server and transmitted to the device 900 via communication system(s) 930.

In some examples, collected flow properties, maps of vasculature, or other information generated by the device 900 may additionally be input to a cloud network and be made available for download by a user's physician. Analyses may also be performed on the collected data, such as estimates of post-surgical recovery, determinations of post-surgical treatment or rehabilitation regimens, and/or efficacy of drug treatment regimens, in the cloud computing network and be made available for download by physicians or clinicians. Further, collected information from individuals or populations of device users may be used by physicians or clinicians in monitoring efficacy of a surgical intervention or other treatment.

Figure 10A:
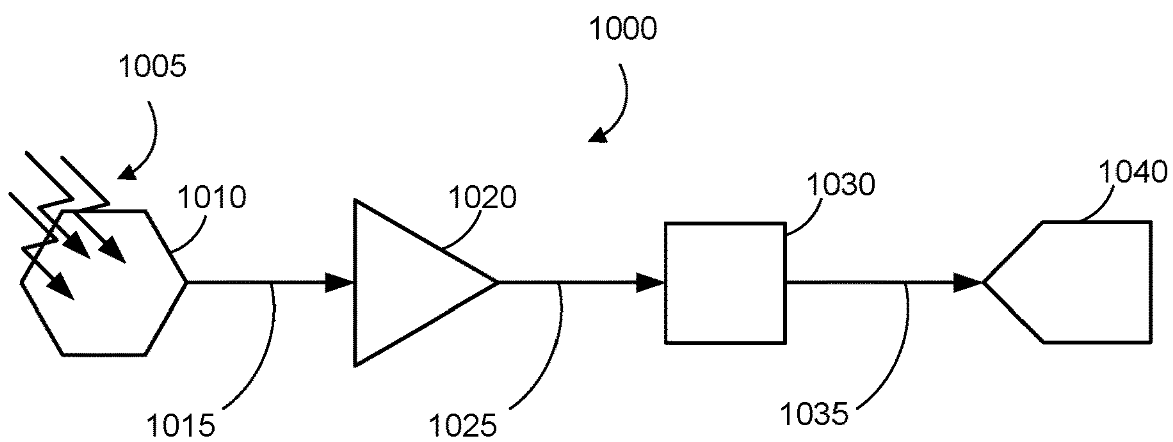
FIG. 10A is a functional block diagram of an example signal processing circuit.
Figure 10B:
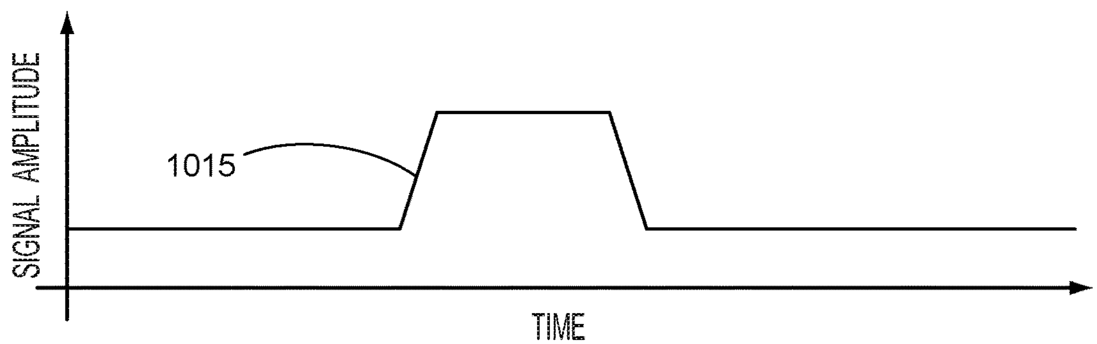
FIG. 10B is an example signal generated by the example signal processing circuit illustrated in FIG. 10A.

FIG. 10A is a functional block diagram of components that could be included in analog frontend circuitry as described herein (e.g., analog frontend circuitry that could be a part of the detection system 910 or of other devices described herein, e.g., 100, 200*a*, 200*b*, 300, 500, 600, 800). The example analog frontend circuitry 1000 illustrated in FIG. 10A includes a light-sensitive element 1010 of a light sensor configured to detect a time-varying pattern of constructive and destructive interference in received light 1005 that is emitted from an environment of interest in response to illumination by a beam of coherent light. The light sensor output 1015 is a signal related to the intensity of the received light 1005. FIG. 10B illustrates an example waveform of the light sensor output 1015 that includes a trapezoidal pulse corresponding to a speckle event. One or more properties of the trapezoidal pulse (e.g., a pulse width, a rise time, a rise rate, a fall time, a fall rate) could be related to a velocity of one or more scatterers in the environment of interest and/or to some other flow properties in the environment of interest.

Figure 10C:
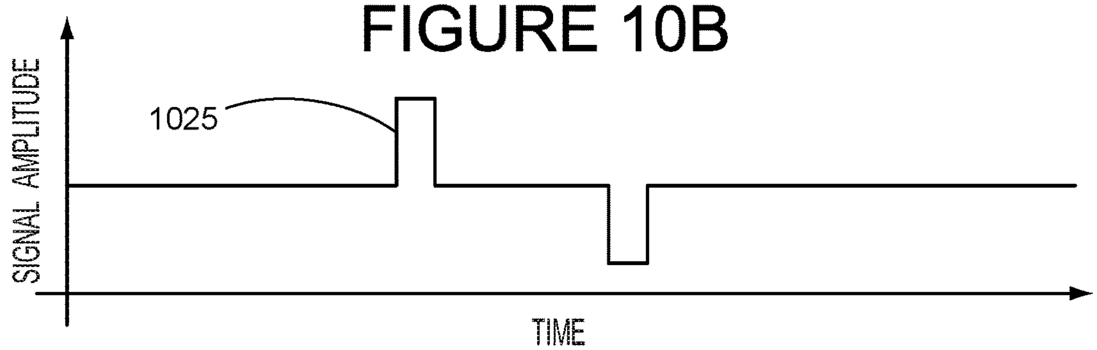
FIG. 10C is an example signal generated by the example signal processing circuit illustrated in FIG. 10A.

The example analog frontend circuitry 1000 additionally includes a differentiator 1020 configured to output a differentiator output 1025 related to a rate of change of the light sensor output 1015. The differentiator could be passive (e.g., an RC and/or RL filter circuit), active (e.g., an op-amp configured with capacitors, resistors, and/or other elements as a differentiator), or some combination thereof. Further, the differentiator output 1025 could be related to the rate of change of the light sensor output 1015; for example, the differentiator 1020 could output a low-passed, rectified, or otherwise altered version of the rate of change of the light sensor output 1015. FIG. 10C illustrates an example waveform of the differentiator output 1025 corresponding to the trapezoidal pulse in the example light sensor output 1015 waveform illustrated in FIG. 10B. The example waveform in FIG. 10C includes a first pulse having an amplitude related to a rise rate of the trapezoidal pulse illustrated in FIG. 10B and a timing corresponding to the rising edge of the trapezoidal pulse. The example waveform in FIG. 10C additionally includes a second pulse having an amplitude related to a fall rate of the trapezoidal pulse illustrated in FIG. 10B and a timing corresponding to the falling edge of the trapezoidal pulse. Note that a differentiator output 1025 waveform corresponding to the example trapezoidal pulse could have a different shape according to the configuration of the differentiator 1020. For example, the differentiator 1020 could be configured to output a signal corresponding to a rectified or otherwise filtered version of the light sensor output 1015 and the example differentiator output 1025 would be changed correspondingly (in this example, the first pulse in the example differentiator output 1025 would be filtered (e.g., would have some larger, finite rise time/fall time, etc.) and would substantially lack to second pulse).

Figure 10D:
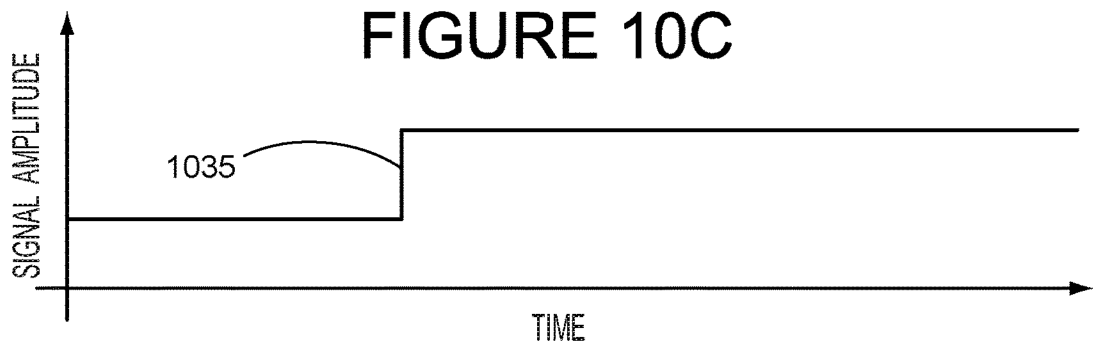
FIG. 10D is an example signal generated by the example signal processing circuit illustrated in FIG. 10A.

The example analog frontend circuitry 1000 additionally includes a peak detector 1030 configured to output a peak detector output 1035 related to a maximum value of the differentiator output 1025 during a specified previous time period. The peak detector 1030 could include passive and active components configured in a variety of ways. In some examples, the peak detector 1030 could include an op-amp, a rectifier, and a capacitor configured to output a peak detector output 1035 corresponding to a maximum value of the differentiator output 1025 in the past. The peak detector 1030 could additionally include a reset electronic switch that could be operated to reset the peak detector 1030, allowing the peak detector output 1035 to correspond to a maximum value of the differentiator output 1025 during a previous time period specified by the operation of the electronic switch. Additionally or alternatively, the peak detector 1030 could include a lossy integrator. FIG. 10D illustrates an example waveform of the peak detector output 1035 corresponding to the positive and negative pulses in the example differentiator output 1025 waveform illustrated in FIG. 10C. The example waveform in FIG. 10D includes a positive step pulse having an amplitude corresponding to the amplitude of the first pulse illustrated in FIG. 10C and a timing corresponding to the rising edge of the first pulse. Note that a peak detector output 1035 waveform corresponding to the example first and second pulses could have a different shape according to the configuration of the peak detector 1030. For example, the peak detector 1030 could include a lossy integrator, and the example peak detector output 1035 would be changed correspondingly (in this example, the step response would decay to lower signal levels over time). In another example, the peak detector 1030 could include an electronic switch operated to periodically reset the peak detector 1030, and the example peak detector output 1035 would be changed correspondingly (in this example, the step response would be replaced with a pulse having a duration corresponding to a difference in time between the timing of the first pulse of the example differentiator output 1025 and the timing of a subsequent operation of the electronic switch).

The peak detector output 1035 could form the output of the example analog frontend circuitry 1000, and could be used to determine flow properties in the environment. As illustrated in FIG. 10A, an analog-to digital (ADC) converter 1040 could be configured and operated to sample the peak detector output 1035 at one or more points in time. For example, the ADC 1040 could be operated by a microcontroller, and the microcontroller could use the output of the ADC 1040 to determine flow properties in the environment of interest (e.g., the microcontroller could determine a flow rate of fluid in a particular portion of the environment corresponding to an amplitude of the peak detector output 1035 measured using the ADC 1040).

VI. Illustrative Methods

Figure 11:
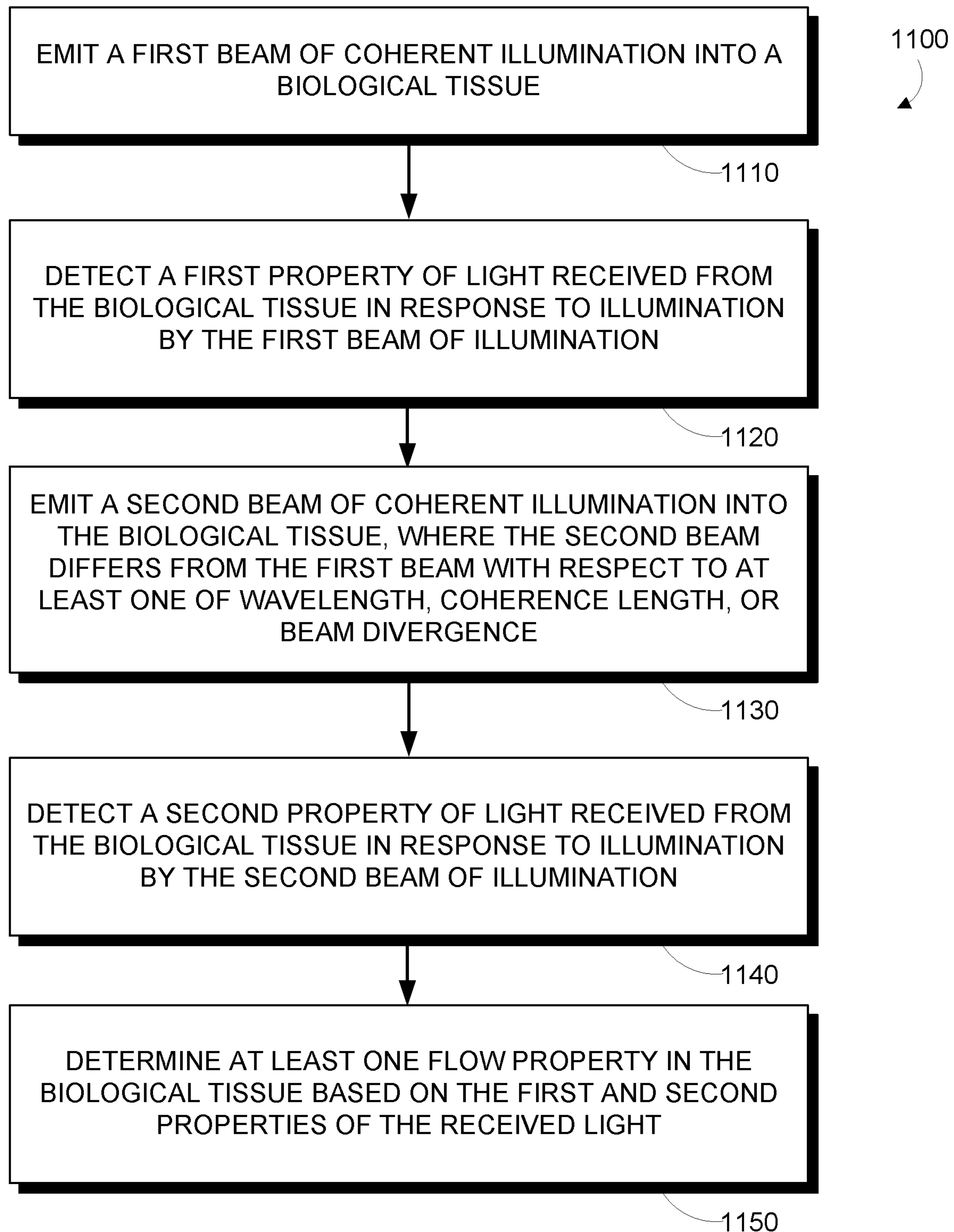
FIG. 11 is a flow chart of an example method.

FIG. 11 is a flowchart of a method 1100 for measuring flow properties in a biological tissue. The method 1100 includes emitting a first beam of coherent illumination into the biological tissue (1110). This could include operating a laser to emit the beam of coherent illumination. The coherent illumination is such that scatterers and other elements in the biological tissue scatter the coherent illumination such that light is responsively emitted from the biological tissue having one or more properties (e.g., time-varying patterns of constructive and destructive interference, wavelengths, differences in wavelength relative to the wavelength of the first beam) that are related at least to flow properties (e.g., blood flows, interstitial fluid flows) within the biological tissue. This can include emitting coherent illumination having a specific wavelength, coherence length, or other properties such that the coherent illumination can be scattered by scatterers disposed in the biological tissue, efficiently transmitted through the biological tissue, or other considerations. Illuminating the biological tissue with a first beam of coherent illumination 1110 can include emitting a beam of coherent illumination having a specified intensity, wavelength, coherence length, spectral linewidth, spectral profile, beam divergence, beam shape, beam angle relative to the biological tissue, polarization, or other property.

The method 1100 additionally includes detecting a first property of light received from the biological tissue in response to illumination by the first beam of illumination (1120). This can include detecting the intensity, wavelength, spectrum, difference in wavelength relative to the wavelength of the first beam of illumination, degree of polarization, orientation of polarization, or other properties of the light emitted from the biological tissue using a light sensor. This can include detecting such properties at a plurality of points in time and/or during a plurality of periods of time. Such periods of time could have one or more specified properties (e.g., a sample rate, an exposure time).

The method 1100 additionally includes emitting a second beam of coherent illumination into the biological tissue, where the second beam differs from the first beam with respect to at least one of wavelength, coherence length, or beam divergence (1130). This could include operating a second laser to emit the second beam of coherent illumination. Emitting the second beam of illumination (1130) could be performed at the same time that the first beam of illumination is emitted (1110) or during a different period of time. Emitting the second beam of coherent illumination (1130) could include operating the same laser used to emit the first beam of illumination (1110) to emit the second beam of illumination by controlling a wavelength, coherence length, beam divergence, or other property of the light emitted by the laser such that the first and second beams differ with respect to the controlled property.

The method 1100 additionally includes detecting a second property of light received from the biological tissue in response to illumination by the second beam of illumination (1140). This can include operating the same light-sensitive element(s) of the light sensor used to detect the first property of light (1120). In examples wherein the first beam of coherent illumination and second beam of coherent illumination are emitted at the same time, detecting a second property of light (1140) could be performed at the same time that the first property of light is detected (1120).

The method 1100 additionally includes determining at least one flow property in the biological tissue based on the first and second properties of the received light (1150). This could include determining one or more flow rates, average flow rates, variances of flow rates, scatterer velocities, distributions of scatterer velocities, or some other flow property or properties. This could include determining one or more flow properties within a specified range of depths within the biological tissue, flow properties in/of a particular tissue type or cell type (e.g., blood) within the biological tissue, or flow properties corresponding to some other location/elements on/within the biological tissue. This could include determining one or more flow properties for a plurality of areas of the biological tissue, for a plurality of volumes within the biological tissue, or according to some other area- or volume-sampling or partitioning of the biological tissue. Determining at least one flow property in the biological tissue (1150) could include determining the at least one flow property based on the first and second detected properties of the received light according to one or more of the methods described elsewhere herein, or a combination of such methods.

The method 1100 could include additional steps or elements in addition to those illustrated in FIG. 11. For example, the method 1100 could include determining a map of vasculature in the biological tissue based on determined flow properties at a plurality of points and or depths within the tissue. The method 1100 could include indicating a determined map of vasculature or other determined information (e.g., flow properties) to a user using a user interface. The method 1100 could include determining a depth of a portion of vasculature or other structure(s) in the biological tissue based on detected properties of received light emitted from the biological tissue as described elsewhere herein. The method 1100 could include determining a level of blood cell oxygenation in particular portions of the biological tissue by, e.g., illuminating the biological tissue with beams of coherent illumination at two or more different wavelengths and detecting properties of light responsively emitted from the biological tissue. The method 1100 could include introducing scatterers into the biological tissue (e.g., injecting, ingesting, transdermally transferring, or otherwise introducing the scatterers into a lumen of vasculature of a human). The method could include operating a robotic surgical system based on determined flow properties in the biological tissue. Additional and/or alternative steps of the method 1100 are anticipated.

VII. Conclusion

Where example embodiments involve information related to a person or a device of a person, the embodiments should be understood to include privacy controls. Such privacy controls include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, flow properties, health states, or other information about the user, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The particular arrangements shown in the Figures should not be viewed as limiting. It should be understood that other embodiments may include more or less of each element shown in a given Figure. Further, some of the illustrated elements may be combined or omitted. Yet further, an exemplary embodiment may include elements that are not illustrated in the Figures.

Moreover, it is particularly noted that while devices, systems, methods, and other embodiments are described herein by way of example as being employed to detect flow properties of biological tissues of a human body, it is noted that the disclosed devices, systems, and methods can be applied in other contexts as well. For example, detection systems configured to detect flow properties of fluid in an environment using coherent light emitters and light sensors as disclosed herein may be included in wearable (e.g., body-mountable) and/or implantable devices. In some contexts, such a detection system is situated to be substantially encapsulated by bio-compatible polymeric material suitable for being in contact with bodily fluids and/or for being implanted. In some examples, such detection systems could be incorporated as part of a robotic surgical system, operated in combination with some other means or method for imaging and/or detecting some other information about biological tissues, or configured and/or operated as part of or in combination with some other system(s).

In other examples, devices, systems, and methods disclosed herein may be applied to measure flow properties of one or more fluids that are not in or on a human body. For example, detection systems disclosed herein may be included devices used to measure flow properties in a fluid of an animal. In another example, devices, systems, and methods disclosed herein may be applied to measure flow properties of an environmental fluid, such as a fluid in a river, lake, marsh, reservoir, water supply, sanitary sewer system, storm sewer system, or the atmosphere. In another example, devices, systems, and methods disclosed herein may be applied to measure flow properties of a fluid that is part of a process, such as a waste treatment process, industrial process, pharmaceutical synthesis process, food preparation process, fermentation process, a microfluidic laboratory or scientific process, or medical treatment process.

Additionally, while various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are contemplated herein.

What is claimed is:

1. A system comprising:

a light source, wherein the light source is configured to (i) emit a first beam of coherent illumination into a biological tissue and (ii) emit a second beam of coherent illumination into the biological tissue, wherein the first beam of coherent illumination and the second beam of coherent illumination differ with respect to at least one of wavelength, coherence length, or beam divergence;

a light sensor configured to receive light from the biological tissue emitted in response to illumination by the light source; and a controller operably coupled to the light sensor and the light source, wherein the controller comprises a computing device programmed to perform controller operations comprising:

emitting the first beam of coherent illumination into the biological tissue using the light source;

detecting, using the light sensor, a first property of light received from the biological tissue in response to illumination by the first beam of coherent illumination, wherein detecting the first property of light received from the biological tissue in response to illumination by the first beam of coherent illumination comprises detecting a time-varying pattern of constructive and destructive interference in light received from blood in the biological tissue;

emitting the second beam of coherent illumination into the biological tissue using the light source;

detecting, using the light sensor, a second property of light received from the biological tissue in response to illumination by the second beam of coherent illumination; and determining a location and a shape of a target structure in the biological tissue based on the first property of light received from the biological tissue in response to illumination by the first beam of coherent illumination and the second property of light received from the biological tissue in response to illumination by the second beam of coherent illumination, wherein the target structure comprises at least one of a tumor, a neoplasm, a cyst, an anastomosis, or an epileptic focus.

2. The system of claim 1, wherein the light source comprises first and second lasers configured to emit the first beam of coherent illumination and the second beam of coherent illumination, respectively.

3. The system of claim 1, wherein the first beam of coherent illumination and the second beam of coherent illumination have respective different first and second wavelengths.

4. The system of claim 3, wherein the light source comprises a tunable laser configured to emit coherent illumination at at least the first wavelength and the second wavelength during respective at least two periods of time.

5. The system of claim 1, wherein the first beam of coherent illumination and the second beam of coherent illumination have respective first and second coherence lengths.

6. The system of claim 5, wherein the light source comprises a laser configured to emit coherent illumination at at least the first coherence length and the second coherence length by detuning a cavity of the laser during respective at least two periods of time.

7. The system of claim 1, wherein the first beam of coherent illumination and the second beam of coherent illumination have respective specified wavelengths, wherein the specified wavelengths are between 400 nanometers and 1000 nanometers.

8. The system of claim 1, wherein the light source is configured to emit the first beam of coherent illumination such that the first beam of coherent illumination is polarized in a first direction, and further comprising a polarization filter.

9. The system of claim 1, wherein the target structure comprises the tumor.

10. A method comprising:

emitting a first beam of coherent illumination into a biological tissue;

detecting a first property of light received from the biological tissue in response to illumination by the first beam of coherent illumination, wherein detecting the first property of light received from the biological tissue in response to illumination by the first beam of coherent illumination comprises detecting a time-varying pattern of constructive and destructive interference in light received from blood in the biological tissue;

emitting a second beam of coherent illumination into the biological tissue, where the second beam of coherent illumination differs from the first beam of coherent illumination with respect to at least one of wavelength, coherence length, or beam divergence;

detecting a second property of light received from the biological tissue in response to illumination by the second beam of coherent illumination; and determining a location and a shape of a target structure in the biological tissue based on the first property of light received from the biological tissue in response to illumination by the first beam of coherent illumination and the second property of light received from the biological tissue in response to illumination by the second beam of coherent illumination, wherein the target structure comprises at least one of a tumor, a neoplasm, a cyst, an anastomosis, or an epileptic focus.

11. The method of claim 10, wherein emitting the first beam of coherent illumination comprises emitting light from a first laser of a light source and emitting the second beam of coherent illumination comprises emitting light from a second laser of the light source.

12. The method of claim 11, wherein emitting the first beam of coherent illumination comprises emitting light from the first laser during a first period of time and wherein emitting the second beam of coherent illumination comprises emitting light from the second laser during a second period of time that is non-overlapping with the first period of time.

13. The method of claim 10, wherein the first beam of coherent illumination and the second beam of coherent illumination are emitted at the same time.

14. The method of claim 10, wherein the first beam of coherent illumination and the second beam of coherent illumination have respective different first and second wavelengths.

15. The method of claim 10, wherein the first beam of coherent illumination and the second beam of coherent illumination have respective different first and second coherence lengths.

16. The method of claim 10, wherein the target structure comprises the tumor.

* * * * *